(12) United States Patent
Hillmyer et al.

(10) Patent No.: US 9,988,393 B2
(45) Date of Patent: Jun. 5, 2018

(54) ISOSORBIDE-BASED POLYMETHACRYLATES

(71) Applicant: REGENTS OF THE UNIVERSITY OF MINNESOTA, Minneapolis, MN (US)

(72) Inventors: Marc A. Hillmyer, Minneapolis, MN (US); Theresa Reineke, Vadnais Heights, MN (US); James Gallagher, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 87 days.

(21) Appl. No.: 15/019,777

(22) Filed: Feb. 9, 2016

(65) Prior Publication Data
US 2016/0229863 A1    Aug. 11, 2016

Related U.S. Application Data

(60) Provisional application No. 62/113,742, filed on Feb. 9, 2015.

(51) Int. Cl.
*C07D 493/04*    (2006.01)
*C08F 122/10*    (2006.01)
(Continued)

(52) U.S. Cl.
CPC .......... *C07D 493/04* (2013.01); *C08F 120/28* (2013.01); *C08F 220/28* (2013.01); *C08F 293/00* (2013.01); *C08F 2438/03* (2013.01)

(58) Field of Classification Search
CPC .... C07D 493/04; C08F 120/28; C08F 220/28; C08F 293/00; C08F 2438/03
(Continued)

(56) References Cited

U.S. PATENT DOCUMENTS

2009/0018300 A1* 1/2009 Bloom .................. C08G 61/12
                                                                527/102
2012/0092426 A1* 4/2012 Chopra ................ C09D 11/101
                                                                347/88
2013/0017492 A1* 1/2013 Hatakeyama ......... G03F 7/0045
                                                                430/285.1

FOREIGN PATENT DOCUMENTS

JP          2004341062 A       12/2004
WO    WO-2004113404 A1    12/2004

OTHER PUBLICATIONS

Mansoori, Yaghoub, et al., "Nanocomposite materials based on isosorbide methacrylate / Cloisite 20A", Polym Int 62, [Online]. Retrieved from the Internet: <URL: www.soci.org, (2013), 280-288.

* cited by examiner

Primary Examiner — Ling Choi
Assistant Examiner — Chun-Cheng Wang
(74) Attorney, Agent, or Firm — Quarles & Brady LLP

(57) ABSTRACT

A monomer comprises the structure

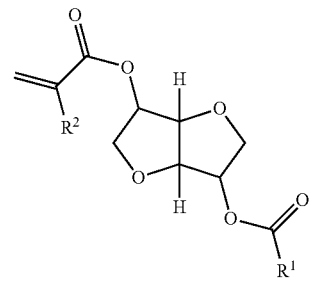

wherein $R^1$ comprises H or a substituted hydrocarbyl or unsubstituted hydrocarbyl, and wherein $R^2$ comprises H, a halide, or a substituted or unsubstituted ($C_1$-$C_4$) hydrocarbyl. A method comprises (a) reacting a dianhydrohexitol precursor having the structure

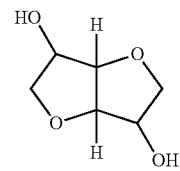

with an acyl-group containing compound having the structure

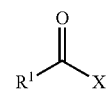

wherein $R^1$ comprises H or a substituted hydrocarbyl or unsubstituted hydrocarbyl, and X comprises a halide, a hydroxyl group, or an acyl group to form an acylated dianhydrohexitol ester intermediate having the structure (Continued)

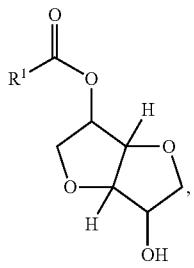

and (b) reacting the acylated dianhydrohexitol ester intermediate with an acrylic-based compound having the structure

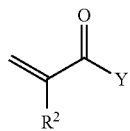

wherein $R^2$ comprises H, a halide, or a substituted or unsubstituted ($C_1$-$C_4$) hydrocarbyl, and Y comprises a halide, a hydroxyl group, or an acyl group, to form a dianhydrohexitol-based monomer having the structure

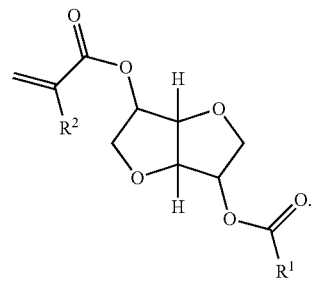

18 Claims, 41 Drawing Sheets

(51) Int. Cl.
*C08F 120/28* (2006.01)
*C08F 220/28* (2006.01)
*C08F 293/00* (2006.01)

(58) Field of Classification Search
USPC .......................................... 526/270
See application file for complete search history.

ISOSORBIDE-BASED POLYMETHACRYLATES

CROSS-REFERENCE TO RELATED APPLICATION

This application claims priority to U.S. Provisional Patent Application 62/113,742, filed on Feb. 9, 2015, which application is incorporated by reference herein in its entirety.

STATEMENT OF GOVERNMENT SUPPORT

This invention was made with government support under CHE-1413862 awarded by the National Science Foundation. The government has certain rights in the invention.

BACKGROUND

Glassy polymers having a relatively high glass transition temperature (referred to herein as "high-$T_g$ polymers"), such as polystyrene and poly(methyl methacrylate), find use in an extremely wide variety of applications, from disposable consumer goods to high performance durable plastics. The glassy high-$T_g$ polymers can also be an important component in block copolymers for use in many applications, such as thermoplastic elastomers and toughening agents.

Nearly all commercially available high-$T_g$ polymers are derived from non-renewable, petroleum-based feedstock. There has been increased interest in renewable chemical feedstocks as they become cost competitive with petroleum-based analogs.

SUMMARY

The present disclosure describes a dianhydrohexitol-based monomer, such as an isosorbide-based monomer, that can be polymerized to form a glassy acrylate-based or methacrylate-based polymer with a relatively high glass transition temperature (e.g., at least about 130° C.) and good thermal stability. The monomer can also be polymerized with a chain-transfer agent (CTA) that can be further reacted to form block copolymers.

The present disclosure describes a monomer comprising the structure

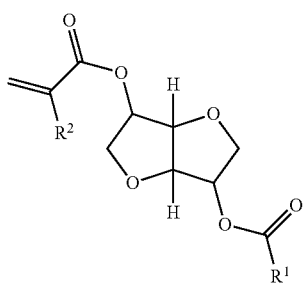

wherein $R^1$ comprises H or a substituted hydrocarbyl or unsubstituted hydrocarbyl, and wherein $R^2$ comprises H, a halide, or a substituted or unsubstituted ($C_1$-$C_4$) hydrocarbyl.

The present disclosure also describes a polymer comprising or copolymer comprising, as a repeating unit, the structure

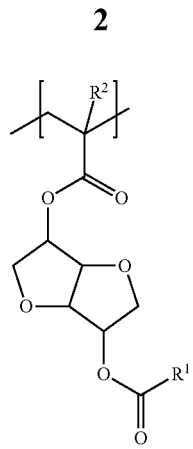

wherein $R^1$ comprises H or a substituted hydrocarbyl or unsubstituted hydrocarbyl, and wherein $R^2$ comprises H, a halide, or a substituted or unsubstituted ($C_1$-$C_4$) hydrocarbyl.

The present disclosure further describes a method comprising:

(a) reacting a dianhydrohexitol precursor having the structure

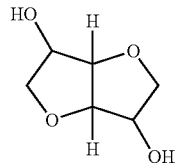

with an acyl-group containing compound having the structure

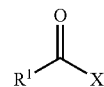

wherein $R^1$ comprises H or a substituted hydrocarbyl or unsubstituted hydrocarbyl, and X comprises a halide, a hydroxyl group, or an acyl group to form an acylated dianhydrohexitol ester intermediate having the structure

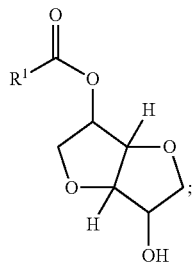

and (b) reacting the acylated dianhydrohexitol ester intermediate with an acrylic-based compound having the structure

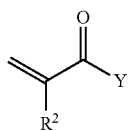

wherein R² comprises H, a halide, or a substituted or unsubstituted (C₁-C₄) hydrocarbyl, and Y comprises a halide, a hydroxyl group, or an acyl group, to form a dianhydrohexitol-based monomer having the structure

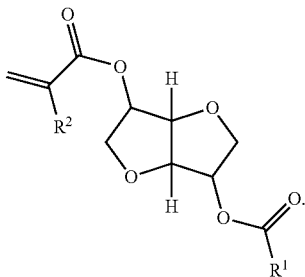

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

The patent or application file contains at least one drawing executed in color. Copies of this patent or patent application publication with color drawing(s) will be provided by the Office upon request and payment of the necessary fee.

DETAILED DESCRIPTION

Figure 1:
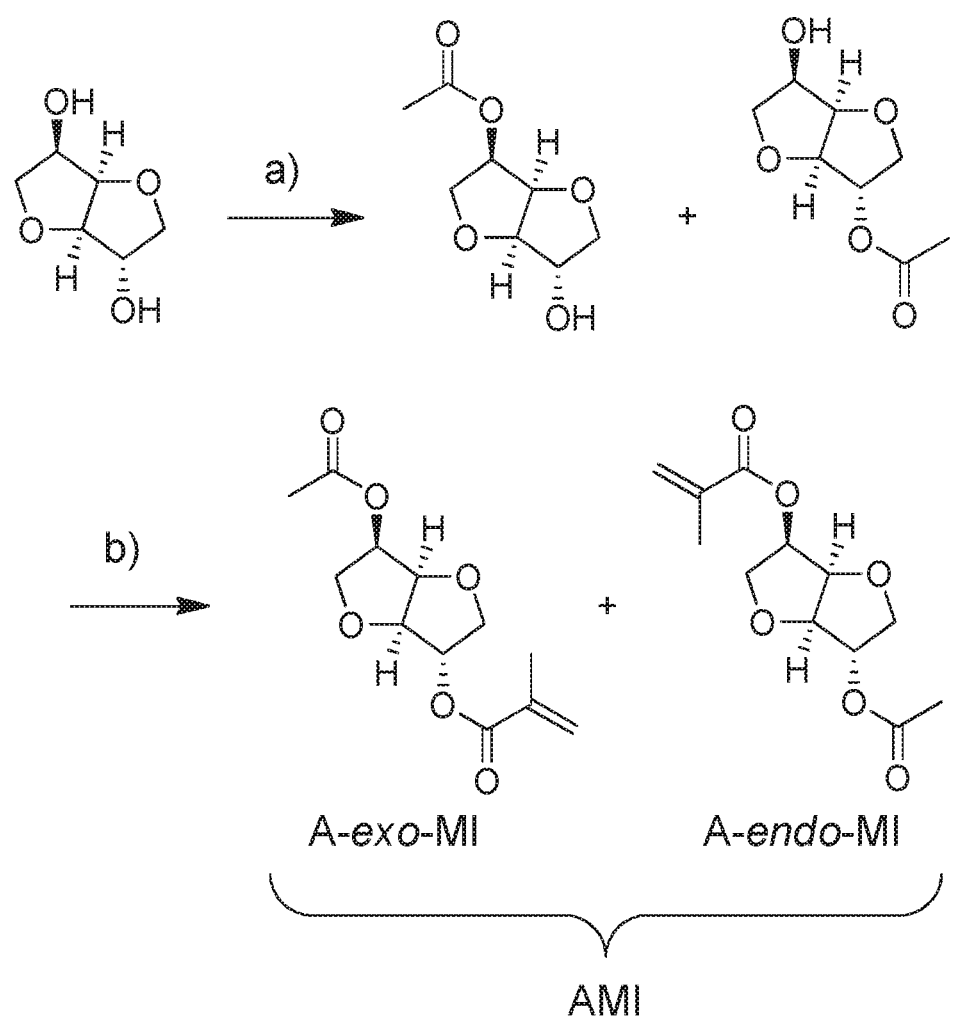
FIG. 1 is a flow diagram of an example reaction scheme for preparing an acetylated methacrylic isosorbide (AMI) monomer.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001."

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety, and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH ($CH_3$), —CH=C($CH_3$)$_2$, —C($CH_3$)=$CH_2$, —C($CH_3$) =CH($CH_3$), —C($CH_2CH_3$)=$CH_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl biphenylenyl, anthracenyl and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "solvent" as used herein refers to a liquid that can dissolve a solid, another liquid, or a gas. Non-limiting examples of solvents are silicones, organic compounds, water, alcohols, ionic liquids, and supercritical fluids.

The term "room temperature" as used herein refers to a temperature of about 15° C. to about 28° C.

The term "standard temperature and pressure" as used herein refers to 20° C. and 101 kPa.

Process of Preparing a Dianhydrohexitol-Based Monomer

In various embodiments, a process of preparing a dianhydrohexitol-based monomer of the structure (I) is described herein.

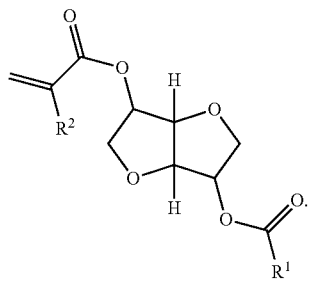

(I)

R$^1$ can be chosen from a substituted or unsubstituted hydrocarbyl, for example any (C$_1$-C$_{30}$) aliphatic or aromatic group. R$^2$ can be chosen from H, a halide (e.g., Cl, Br, I, or F), or a substituted or unsubstituted hydrocarbyl, such as a (C$_1$-C$_{10}$) hydrocarbyl, for example a (C$_1$-C$_4$) hydrocarbyl. In an example, R$^2$ is chosen from a methyl group (—CH$_3$) or H, e.g., so that the dianhydrohexitol-based monomer comprises an acrylate group or a methacrylate group.

Recent improvements in the conversion of sugar alcohols, for example hexitols such as sorbitol or mannitol, to dianhydrohexitols, such as isosorbide, isoidide, and isomannide (see structures (III), (IV), and (V) below) have made dianhydrohexitols such as isosorbide a promising building block for biorenewable polymers on the commercial scale. For example, isosorbide is often compared to bisphenol A due to its rigid bicyclic structure and its diol functionality. Isosorbide has been incorporated into a wide variety of step growth polymers, including polyesters, polycarbonates, polyethers, and polyurethanes.

Despite its promise, the dianhydrohexitols have not typically been incorporated into linear chain growth polymerized polymers. Linear-chain growth can be an appealing building block because the construction of polymers with designed architectures is more easily accomplished via chain growth mechanisms. Various options for functionalizing the hydroxyl groups of dianhydrohexitols have been attempted, such as esterification, etherification, carbonylation, and tosylation. Due to the relatively poor reactivity of secondary alcohols, esterification methods have typically used auxiliary reactants. For example, one method of acetylating isosorbide can use acetic acid, N,N dicyclohexylcarbodiimide, and catalytic 4-dimethylaminopyridine (i.e., a Steglich esterification). Acetylation by this method occurs predominantly (e.g., about 60% of the product mixture) at the less sterically encumbered exo position of the isosorbide molecule due to the steric bulk of the O-acyl isourea intermediate. An alternative approach for acetylation can use acetic anhydride and catalytic lead (II) oxide. This method favors acetylation (about 80% isolated yield) at the endo position of the isosorbide molecule. Although more sterically hindered due to being on the interior of the puckered bicyclic structure, the alcohol in the endo position is more nucleophilic due to intramolecular hydrogen bonding with the ethereal oxygen of the opposite tetrahydrofuran ring. However, this strategy requires the use of a toxic heavy metal salt.

Likewise, synthesis of methacrylic dianhydrohexitol has been reported via Steglich esterification methods, via the use of methacrylic anhydride and stoichiometric equivalent of an amine base, or methacryloyl chloride and an equivalent of triethylamine. Although these approaches are effective, the use of relatively large amounts of auxiliary reactants may be less than ideal from a green chemistry point of view.

The dianhydrohexitol-based monomer of structure (I) can be prepared by converting a dianhydrohexitol precursor having the structure (II).

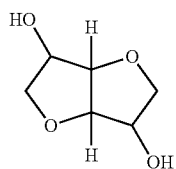
(II)

In an example, the dianhydrohexitol precursor can be a composition comprising at least one of three stereoisomers: isosorbide having the structure (III); isomannide having the structure (IV); and isoidide having structure (V).

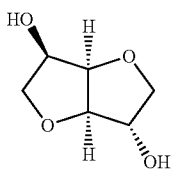
(III)

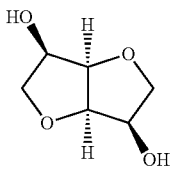
(IV)

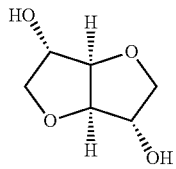
(V)

The dianhydrohexitol precursor (e.g., isosorbide, isomannide, or isoidide) can be reacted with an acyl-group containing compound having the structure (VI), such as an acyl anhydride having the structure (VI):

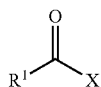
(VI)

where $R^1$ is as described above with respect to structure (I), and X comprises a halide (e.g., Cl, Br, F, or I, to form an acyl halide), a hydroxyl group, e.g., forming a carboxylic acid as in structure (VII), or another acyl group, e.g., to form an anhydride as in structure (VIII).

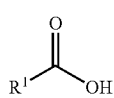
(VII)

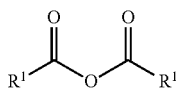
(VIII)

Each $R^1$ in structure (VIII) can be independently selected as described above with respect to structure (I). In an example, each $R^1$ group comprises a methyl ($CH_3$) group (e.g., acetic anhydride, acetic acid, or an acetyl halide). The dianhydrohexitol precursor and the acyl-group containing compound react to form an acylated dianhydrohexitol ester intermediate having the structure (IX):

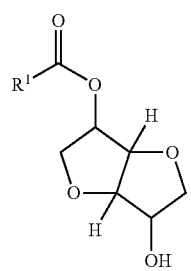
(IX)

in which $R^1$ is as described above with respect to structure (I). In examples where $R^1$ is a methyl group and the dianhydrohexitol precursor is isosorbide, the acylated dianhydrohexitol ester intermediate is an acetylated isosorbide ester intermediate having the structure (X):

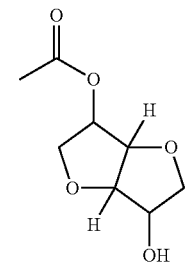
(X)

The isosorbide molecule includes an exo hydroxyl group and an endo hydroxyl group. Therefore, the acetylated isosorbide ester intermediate, can be formed with the acetate group in the exo position or in the endo position. For example, for the acetylated isosorbide ester intermediate shown as structure (X), the acetate group can be in the exo position or in the endo position, and the resulting acetylated isosorbide ester intermediate can comprise a mixture of isosorbide exo-acetate having structure (XI) and isosorbide endo-acetate having structure (XII).

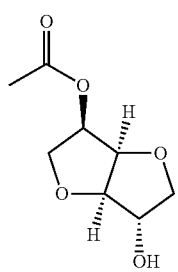

(XI)

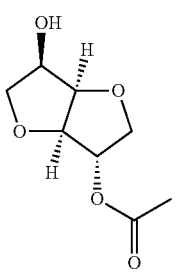

(XII)

Similarly, if the dianhydrohexitol precursor comprises isomannide having two exo hydroxyl groups, then the resulting acylated dianhydrohexitol ester intermediate will comprise only exo acyl groups. If the dianhydrohexitol precursor comprises isoidide having two endo hydroxyl groups, then the acylated dianhydrohexitol ester intermediate will comprise only endo acyl groups.

The dianhydrohexitol precursor can be reacted with the acyl-group containing compound in the presence of a catalyst. In an example, the reaction can be performed in a solvent such as acetonitrile. The catalyst can comprise any catalyst that can catalyze esterification of the dianhydrohexitol precursor such as a Lewis acid catalyst, for example zinc chloride ($ZnCl_2$), boron trifluoride ($BF_3$), tin (IV) chloride ($SnCl_4$), aluminum chloride ($AlCl_3$), or titanium tetrachloride ($TiCl_4$). In an example, a triflate-containing catalyst can be used, such as a lanthanide triflate, for example scandium (III) triflate ("$Sc(OTf)_3$"), or other triflate-containing catalysts such as bismuth (III) triflate ("Bi$(OTf)_3$"), $Sc(OTf)_3$ and other lanthanide triflates have been found to have relatively high stability towards air and water, and therefore can be handled under ambient atmosphere, do not require anhydrous reaction conditions, and can be easily recycled and reused without loss of activity. Other examples of catalysts or additives that can be used for esterification of dianhydroxitols include, but are not limited to: sulfonic acids such as methane sulfonic acid, benzene sulfonic acid, or p-toluene sulfonic acid; phosphoric acids; acetates such as sodium acetate, potassium acetate, ammonium acetate, calcium acetate, barium acetate, lead acetate, or cobalt acetate; propionates such as sodium propionate; butyrates such as ammonium butyrate or sodium isobutyrate; capronates such as potassium capronate; carbonates such as potassium carbonate, sodium carbonate, or calcium carbonate; hydrides such as sodium hydride, potassium hydride, or calcium hydride; alkylates such as sodium methylate, sodium ethylate, or potassium tert-butylate; metal oxides such as aluminum oxide, calcium oxide, or lead oxide (PbO); hydroxides such as sodium hydroxide, potassium hydroxide, or calcium hydroxide; amine containing compounds such as trimethylamine, 4-dimethylaminopyridine, or triphenylamine; ammonium containing compounds such as cetyl trimethyl ammonium bromide, tetrabutyl ammonium hydrogen sulfate, benzyl triethyl ammonium hydrogen sulfate, benzyl triethyl ammonium chloride, tetraethyl ammonium hydroxide; or a phosphonium containing compounds such as benzyl triphenyl phosphonium bromide. Further examples of catalysts are listed in U.S. Pat. No. 4,371,703, issued on Feb. 1, 1983, the disclosure of which is incorporated herein as if reproduced in its entirety.

In the step of reacting the dianhydrohexitol precursor with an acyl-group containing compound to form the acylated dianhydrohexitol ester intermediate, $Sc(OTf)_3$ was found to be an exceptionally active catalyst. For example, full consumption of acetic anhydride (1 mol eq.) when reacting with isosorbide occurred in less than 10 minutes at room temperature using a catalyst loading of 0.05 mol. % relative to the reactants. By comparison, acetylation of isosorbide with acetic anhydride and 2 mol. % lead (II) oxide catalyst range from about 2 hours to about 20 hours. Analysis of the crude product mixture by $^1H$ NMR spectroscopy indicated that the endo hydroxyl was the preferred site for acetylation. In one example, the ratio of endo-acetate to exo-acetate in the product mixture was about 4:1, such as about 4.2:1.

In some examples, a monoacetylated isosorbide is preferred over a diacetylated isosorbide, e.g., one or both of the monoacetylated isosorbide ester intermediates of structure (XI) or structure (XII) being preferred over a diacetylated isosorbide ester intermediate where both the endo and the exo hydroxyl groups of isosorbide (structure (III)) are converted to acetate ester groups upon reaction with the acyl-group containing compound having the structure (VI). In some examples, one of the stereoisomers of the acylated dianhydrohexitol ester intermediate (e.g., the stereoisomers of structure (XI) and structure (XII)) is preferred over the other stereoisomer. In an example, the isosorbide endo-acetate having structure (XII) is preferred over the exo-acetate having structure (XI).

In an example, a preferred isosorbide intermediate formed from the reaction of isosorbide with the acyl-group containing compound having the structure (VI) is isolated or purified with respect to the other potential products of the reaction and from unreacted isosorbide. In an example, one or more preferred isosorbide intermediates, e.g., the isosorbide endo-acetate having structure (XII), is isolated or purified with respect to other reaction products, e.g., the isosorbide exo-acetate having structure (XI) and diacetylated isosorbide ester, and unreacted isosorbide by one or more isolation or separation operations. Examples of isolation or separation operations used to isolate or purify the preferred one or more isosorbide intermediates include, but are not limited to column chromatography and distillation, such as reactive distillation. In an example, the preferred one or more isosorbide intermediates are isolated or purified via reactive distillation, such as the type of reactive distillation described in Stoss et al., Regioselektive Acylierung von 1,4:3,6-Dianhydro-D-glucit ("Regioselective alkylation of 1,4:3,6-dianhydro-D-glucitol"), Synthesis (1987), 174-76, available online at https://www.thieme-connect.com/products/ejournals/abstract/10.1055/s-1987-27878, the entire disclosure of which is incorporated by reference as if reproduced herein. In an example, reactive distillation includes contacting the reaction product mixture with a hydroxide, such as potassium hydroxide, and heating the resulting mixture in a distillation column set at about 100 mbar. In an example, the reactive distillation improves the selectivity toward a preferred monoacetylated isosorbide intermediate, such as the isosorbide endo-acetate having structure (XII), e.g., so that the preferred monoacetylated isosorbide intermediate has a higher concentration in the reaction mixture than it would have had without the distillation.

The isolated or purified carboxylated dianhydrohexitol ester intermediate can then be reacted with an acrylic-based compound having the structure (XIII)

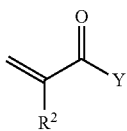
(XIII)

where R² is as described above with respect to structure (I), and Y comprises a halide (e.g., Cl, Br, F, or I, to form an acrylic-based halide), a hydroxyl group, e.g., forming an acrylic-based acid as in structure (XIV), or another acyl group, e.g., to form an acrylic-based anhydride as in structure (XV).

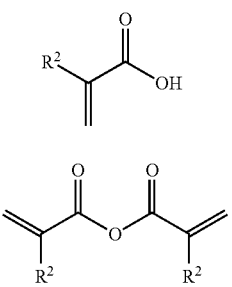
(XIV)

(XV)

Each R² can be independently selected as described above with respect to structure (I), e.g., an H or a methyl group (—CH₃). In an example, each R² group comprises a methyl group (e.g., methacrylic anhydride, methacrylic acid, or a methacryloyl halide).

The acylated dianhydrohexitol ester intermediate and the acrylic-based compound react to form the dianhydrohexitol-based monomer shown above in structure (I). In some examples, R¹ and R² are each methyl groups and the dianhydrohexitol precursor is isosorbide and, therefore, the dianhydrohexitol-based monomer is an acetylated methacrylic isosorbide (referred to herein as "AMI") having the structure (XVII).

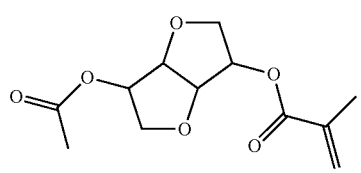
(XVII)

In some examples, R¹ is a methyl group (—CH₃) and R² is a hydrogen atom (—H) and the dianhydrohexitol precursor is isosorbide and, therefore, the dianhydrohexitol-based monomer is an acetylated acrylic isosorbide (referred to herein as "AAI") having the structure (XVIII).

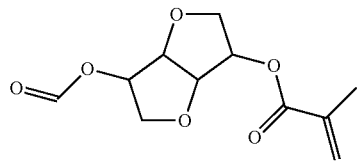
(XVIII)

As noted above, the isosorbide molecule includes an exo hydroxyl group and an endo hydroxyl group, and, as further noted above, the acetylated isosorbide ester intermediate can be formed with the acetate group in the exo position or in the endo position (see structure (XI) and (XII) above). Similarly, the AMI monomer can be formed with the acetate group in the exo position and the methacrylic group in the endo position, referred to herein as acetate-exo-methacrylic isosorbide or "A-exo-MI," having structure (XIX), or the AMI monomer can be formed with the acetate group in the endo position and the methacrylic group in the exo position, referred to herein as acetate-endo-methacrylic isosorbide or "A-endo-MI," having structure (XX).

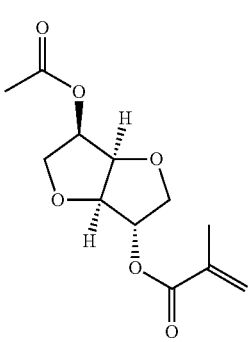
(XIX)

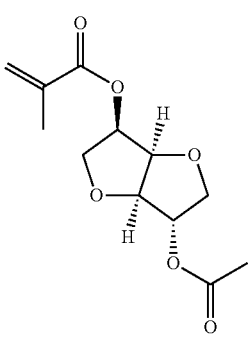
(XX)

Similar exo- and endo-structures are formed from the AAI monomer of structure (XVIII).

If the dianhydrohexitol precursor comprises isomannide having two exo hydroxyl groups, then the resulting dianhydrohexitol-based monomer will comprise an exo carboxylate group and an exo acrylic or methacrylic group. If the dianhydrohexitol precursor comprises isoidide having two endo hydroxyl groups, then the dianhydrohexitol-based monomer will comprise an endo carboxylate groups and an endo acrylic or methacrylic group.

The acylated dianhydrohexitol ester intermediate and the acrylic-based compound react in the presence of a catalyst. In an example, the reaction can be performed in a solvent such as acetonitrile or dichloromethane (CH₂Cl₂). The catalyst can comprise any of the catalysts described above for the reaction between the dianhydrohexitol monomer and the acyl-group containing compound, such as a Lewis acid catalyst, for example a triflate-containing catalyst, such as scandium (III) triflate ("Sc(OTf)$_3$"). Sc(OTf)$_3$ and other lanthanide triflates have relatively high stability towards air and water, and therefore can be handled under ambient atmosphere, do not require anhydrous reaction conditions, and can be easily recycled and reused without loss of activity. Other catalysts can be used for the reaction between the acylated dianhydrohexitol ester intermediate and the acrylic-based compound, such as the catalyst types described above, including, but not limited to other Lewis acid catalysts such as ZnCl$_2$, BF$_3$, SnCl$_4$, AlCl$_3$, or TiCl$_4$; sulfonic acids; phosphoric acids; acetates; propionates; butyrates; capronates; carbonates; hydrides; metal oxides; hydroxides; amine-containing compounds; ammonium-containing compounds; or phosphonium-containing compounds. Specific nonlimiting examples of each type of catalyst are listed above, and can be used for the reaction between the acylated dianhydrohexitol ester intermediate and the acrylic-based compound as well. In an example, the catalyst used for the reaction between the acylated dianhydrohexitol ester intermediate and the acrylic-based compound is the same catalyst that is used for the reaction between the dianhydrohexitol precursor and the acyl-group containing compound to form the acylated dianhydrohexitol ester intermediate as described above (e.g., Sc(OTf)$_3$). In an example, the catalyst used for the reaction between the acylated dianhydrohexitol ester intermediate and the acrylic-based compound is a different catalyst from that used for the reaction between the dianhydrohexitol precursor and the acyl-group containing compound to form the acylated dianhydrohexitol ester intermediate as described above, such as an example where a catalyst for the reaction between the dianhydrohexitol precursor and the acyl-group containing compound to form the acylated dianhydrohexitol ester intermediate is a sulfonic acid such as one or more of methane sulfonic acid, benzene sulfonic acid, or p-toluene sulfonic acid and a catalyst for the reaction between the acylated dianhydrohexitol ester intermediate and the acrylic-based compound is an amine containing compounds such as trimethylamine, 4-dimethylaminopyridine, or triphenylamine.

In an example, Sc(OTf)$_3$ was found to be an active catalyst for the reaction between the acylated dianhydrohexitol ester intermediate and the acrylic-based compound, as it was with the previous step of reacting the dianhydrohexitol precursor with the dianhydrohexitol. For example, complete conversion of methacrylic anhydride (0.97 mol eq.) when reacting with acetylated isosorbide occurred in about 4 hours at room temperature using a catalyst loading of 1 mol. % relative to the isosorbide. It is believed that the reduced reactivity relative to the reaction of isosorbide with acetic anhydride, described above, is attributable to the difference in sterics between acetic anhydride and methacrylic anhydride. Additionally, the majority of hydroxyl groups available for functionalization in the second step are located in the less active (but more sterically accessible) exo position.

The method of forming the dianhydrohexitol-based monomer (e.g., AMI or AAI) can also be reversed relative to what is described above. The method described above includes first reacting the dianhydrohexitol precursor (e.g., isosorbide) with the acyl-group containing compound (e.g., acetic anhydride) to form an acylated dianhydrohexitol ester intermediate (e.g., the acetylated isosorbide ester of structure (X)), and then reacting the acylated dianhydrohexitol ester intermediate with the acrylic-based compound (e.g., methacrylic anhydride or acryloyl chloride) to form the dianhydrohexitol-based monomer (e.g., AMI or AAI). However, the method could be performed by first reacting the dianhydrohexitol precursor (e.g., isosorbide) with the acrylic-based compound (e.g., methacrylic anhydride or acryloyl chloride) to form an acrylic-based dianhydrohexitol ester intermediate having the structure (XXI):

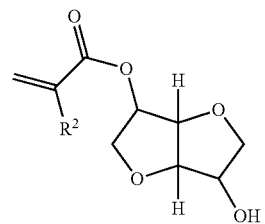

(XXI)

where R$^2$ can be as defined above with respect to structure (I), and then reacting the acrylic-based dianhydrohexitol ester intermediate with the acyl-group containing compound (e.g., acetic anhydride) to form the dianhydrohexitol-based monomer (e.g., AMI or AAI). The steps can use the same catalyst and reaction conditions as described for the method steps described above.

Polymerization of Dianhydrohexitol-Based Monomer

The dianhydrohexitol-based monomer of structure (I) can be polymerized via linear chain growth polymerization, such as free-radical polymerization. Previously, isosorbide had been incorporated into step growth polymers, such as polyesters, polycarbonates, polyethers, and polyurethanes. However, an isosorbide-based monomer, or other dianhydrohexitol-based monomers, that can be polymerized by linear chain growth polymerization can be desirable because the construction of polymers with designed architectures can be more easily accomplished via chain growth mechanisms. The dianhydrohexitol-based monomer described above is a monovinyl monomer that can be used in chain-growth polymerization.

The dianhydrohexitol-based monomer of structure (I) can be polymerized, for example, by free-radical polymerization. The dianhydrohexitol-based monomer can be put into a solution with a solvent, such as chloroform (CHCl$_3$), in the presence of a free-radical initiator. Any free-radical initiator that can initiate free-radical polymerization of the dianhydrohexitol-based monomer can be used, such as a halogen radical initiator, an azo-based initiator, a peroxide initiator, or a disulfide initiator. In an example, an azo-based initiator, such as azobisisobutyronitrile (AIBN), is used to initiate polymerization of the dianhydrohexitol-based monomer (e.g., AMI or AAI). The resulting dianhydrohexitol-based polymer can have the structure (XXII) as a repeating unit.

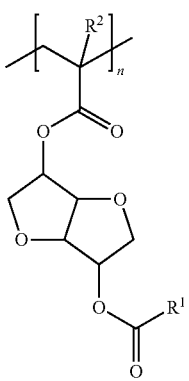

(XXII)

In an example, n (e.g., the number of repeating units) is from about 2 to about 100,000,000, such as from about 10 to about 1000, such as from about 40 to about 400. In examples where the dianhydrohexitol-based monomer is AMI, the resulting polymer is referred to herein as poly-acetylated methacrylic isosorbide ("PAMI") and has the structure (XXIII).

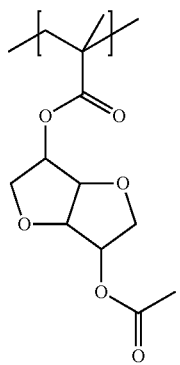

(XXIII)

In examples where the dianhydrohexitol-based monomer is AAI, the resulting polymer is referred to herein as poly-acetylated acrylic isosorbide ("PAAI") and has the structure (XXIV).

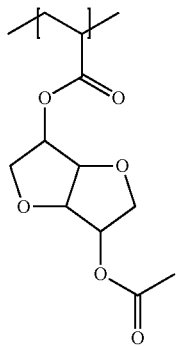

(XXIV)

The resulting dianhydrohexitol-based polymers were found to have relatively high glass-transition temperatures ($T_g$). In an example, the dianhydrohexitol-based polymer, such as PAMI or PAAI, had a $T_g$ of at least about 90° C., for example at least about 91° C., at least about 92° C. at least about 93° C., at least about 94° C., at least about 95° C., at least about 96° C., at least about 97° C., at least about 98° C., at least about 99° C., at least about 100° C. at least about 101° C., at least about 102° C. at least about 103° C., at least about 104° C., at least about 105° C. at least about 106° C. at least about 107° C., at least about 108° C., at least about 109° C., at least about 110° C. at least about 111° C. at least about 112° C., at least about 113° C., at least about 114° C. at least about 115° C., at least about 116° C., at least about 117° C., at least about 118° C., at least about 119° C., at least about 120° C., at least about 121° C. at least about 122° C., at least about 123° C. at least about 124° C., at least about 125° C., at least about 126° C., at least about 127° C., at least about 128° C. at least about 129° C. at least about 130° C., at least about 131° C., at least about 132° C. at least about 133° C. at least about 134° C., at least about 135° C., at least about 136° C., at least about 137° C., at least about 138° C. at least about 139° C., or at least about 140° C. or more, such as from about 90° C. to about 140° C. In an example, a dianhydrohexitol-based polymer, such as an isosorbide-based polymer (e.g., PAMI or PAAI), can have a $T_g$ as high as 130° C. or more. As reported in the literature, a similar traditionally-prepared methacrylate polymer, polymethylmethacrylate (PMMA), has a glass transition temperature of only about 110° C. Without being bound to any theories, it is believed that the dianhydrohexitol-based polymers described herein have a $T_g$ that is even higher than PMMA because of reduced polymer flexibility caused by additional steric bulk of the pendant dianhydrohexitol carboxylate groups (e.g., isosorbide acetate groups for PAMI and PAAI).

The dianhydrohexitol-based polymers can also have a relatively high degradation temperature ($T_d$). In an example, the dianhydrohexitol-based polymer can have a $T_d$ under nitrogen gas ($N_2$) of at least about 230° C., for example at least about 231° C., about 232° C., about 233° C., about 234° C., about 235° C., about 236° C. about 237° C. about 238° C., about 239° C., about 240° C., about 241° C., about 242° C., about 243° C. about 244° C., about 245° C., about 246° C. about 247° C., about 248° C., about 249° C., about 250° C., about 255° C. about 260° C. about 265° C., about 270° C. about 280° C., about 285° C., about 290° C. about 295° C. about 300° C., about 305° C., about 310° C. about 315° C. about 320° C., about 325° C., about 330° C., about 331° C., about 332° C., about 333° C. about 334° C., or about 335° C. or more. In an example, the dianhydrohexitol-based polymer can have a $T_d$ under air of at least about 200° C., for example at least about 201° C., about 202° C. about 203° C., about 204° C., about 205° C., about 206° C., about 207° C. about 208° C. about 209° C., about 210° C., about 211° C., about 212° C., about 213° C., about 214° C., about 215° C., about 216° C., about 217° C. about 218° C., about 219° C., about 220° C. about 225° C., about 230° C., about 235° C., about 240° C., about 245° C. about 250° C. about 255° C., about 260° C., about 265° C., about 270° C., about 275° C. about 280° C. about 281° C., about 282° C., about 283° C., about 284° C., about 285° C. about 286° C. about 287° C., about 288° C., about 289° C., or at least about 290° C. or more. The $T_d$ of the dianhydrohexitol-based polymers described herein is comparable to those reported for PMMA of about 230° C.

As described in more detail below in the Examples, in the case of some isosorbide-based monomers, such as AMI, there was no significant difference in reactivity between endo acylated isosorbide-based monomers and exo acylated isosorbide-based monomers. There was also no significant differences in $T_d$ or $T_g$ between exo isosorbide-based polymers or endo isosorbide-based polymers, or between either regioisomer and a polymer chain comprising both endo and exo isosorbide-based monomers, indicating that the regiochemistry of substituents on isosorbide-based monomers does not alter the thermal properties of the resulting polymer. Based on these results, in at least some examples, both the isosorbide-based monomer and the isosorbide-based polymer can be prepared without the need for careful consideration of isomer composition in the final product.

Chain-Transfer Polymerization of Dianhydrohexitol-Based Monomer

The dianhydrohexitol-based monomer of structure (I) can also be polymerized by controlled radical polymerization into block copolymers, for example by polymerizing the dianhydrohexitol-based monomer by reversible addition-fragmentation chain transfer (RAFT) polymerization. The thermal stability and high $T_g$ of the dianhydrohexitol-based polymer of structure (XXII) (such as the PAMI of structure (XXIII) or the PAAI of structure (XXIV)), make it a promising sustainable candidate for a hard component of block copolymer systems.

The dianhydrohexitol-based monomer of structure (I) can be polymerized with a chain-transfer agent ("CTA") via RAFT. The CTA can be any class of CTA that can provide for RAFT polymerization of dianhydrohexitol-based monomers, such as AMI or AAI. In an example, the CTA can comprise a dithiobenzoate, such as 4-cyano-1-hydroxypent-4-yl dithiobenzoate. In an example, the CTA that was found to provide for the highest monomer conversion of the AMI monomer while providing a suitable low dispersity ($Ð$) was 4-cyano-4-(phenylcarbonothioylthio)pentanoate (referred to herein as "HO-CPAD"), which has the structure (XXV).

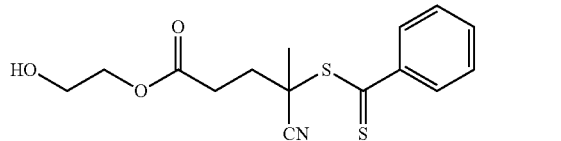

(XXV)

HO-CPAD is a structural analogue to 4-cyano-1-hydroxy-pent-4-yl dithiobenzoate. In an example, HO-CPAD is synthesized by Steglich esterification of the commercially available 4-cyano-4-(phenylcarbonothioylthio)pentanoic acid with excess ethylene glycol. The HO-CPAD can then be purified from the reaction products, such as by column chromatography.

Another CTA that has been found to be useful for RAFT polymerization of dianhydrohexitol-based monomer of structure (I) is 3,5-bis(2-dodecylthiocarbonothioylthio-1-oxopropoxy)benzoic acid (referred to herein as "BTCBA"), which has the structure (XXVI).

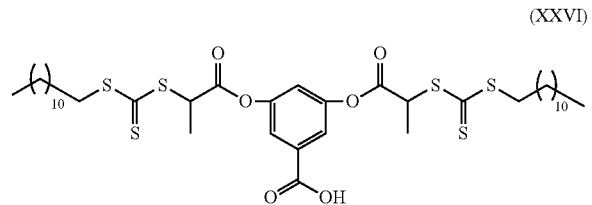

(XXVI)

The dianhydrohexitol-based monomer is polymerized by RAFT polymerization by reacting the CTA, e.g., HO-CPAD or BTCBA, with the dianhydrohexitol-based monomer in a solvent, such as dimethylformamide ("DMF"), and with a free-radical initiator, such as AIBN, to initiate polymerization of the dianhydrohexitol-based monomer.

In an example, RAFT polymerization of AMI as the dianhydrohexitol-based monomer and HO-CPAD as the CTA results in a poly-AMI (PAMI)-CTA polymer, referred to herein as "PAMI-CTA," having the structure (XXVII):

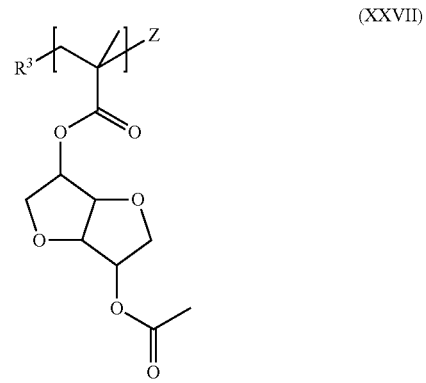

(XXVII)

where $R^3$ is the free-radical leaving group fragment of HO-CPAD, defined by structure (XXVIII), and Z is the dithiobenzoate group fragment of HO-CPAD, defined by structure (XXIX).

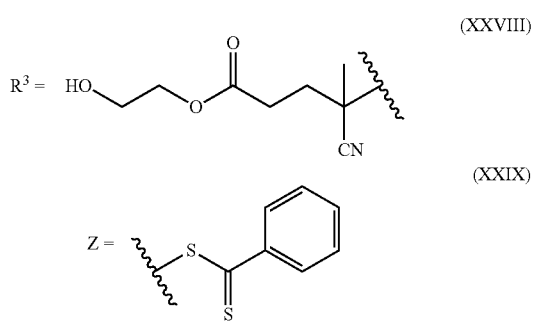

(XXVIII)

(XXIX)

The use of HO-CPAD as a CTA can result in functional polymers with a hydroxyl end group (i.e., the left-most hydroxyl group in structure (XXVIII)), which can be particularly useful due to the synthetic versatility of a hydroxyl group (e.g., in the preparation of block copolymers containing mechanistically differentiated components). For example, when the dianhydrohexitol-based monomer, such as AMI, is polymerized by RAFT polymerization, for example using AIBN as the free-radical initiator in a solvent such as dimethylformamide ("DMF"), the HO-CPAD molecule becomes separated into $R^3$ and Z as described above.

The resulting dianhydrohexitol-based CTA polymer can have similar thermal stability under $N_2$ and air as the dianhydrohexitol-based monomer or the conventional free radical polymerized dianhydrohexitol-based polymer. For example, PAMI-CTA was found to have a $T_d$ in $N_2$ of about ° C. 255 and a $T_d$ in air of about 252° C. $T_g$ values of the dianhydrohexitol-based polymer and CTA are also consistent with those of the dianhydrohexitol-based polymer along. For example, PAMI-CTA had a $T_g$ from about 91° C.

to about 108° C. depending on molecular weight ($M_n$) of the sample, and a linear regression of $T_g$ vs. $1/M_n$ data based on the Flory-Fox equation. $T_g$ was essentially constant at 130° C. for PAMI at molar masses >55 kg mol$^{-1}$, so that the $T_g$ values of the PAMI-CTA are in good agreement with the $T_g$ values observed for PAMI and PA-endo-MI prepared by free-radical polymerization.

A block copolymer can be formed by chain extension polymerization of the dianhydrohexitol-based CTA polymer with another polymer. Examples of the block copolymer include but are not limited to: low glass transition temperature polymers, including low glass transition temperature aliphatic polyesters such as polycaprolactone, poly(methyl caprolactone), poly(beta methyl valerolactone), and poly(deltadecalactone); acrylate polymers, such as poly-n-butyl acrylate, polymethyl acrylate, and polyethyl acrylate; and methacrylate polymers such as polybutyl methacrylate and polyhexyl methacrylate. For example, it is believed that poly-n-butyl acrylate (PnBA) can be useful as a rubbery counterpart to the dianhydrohexitol-based polymer (e.g., PAMI) due to its low $T_g$ of about –50° C. as well as recent developments towards the commercial production of biobased acrylates. In an example, chain extension polymerization of PAMI-CTA (structure (XXVII)) with n-butyl acrylate having structure (XXX)

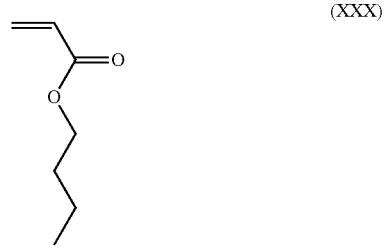

(XXX)

results in a poly acetylated methacrylic isosorbide-block-poly-n-butyl acrylate, referred to herein as "PAMI-b-PnBA," having the structure (XXXI):

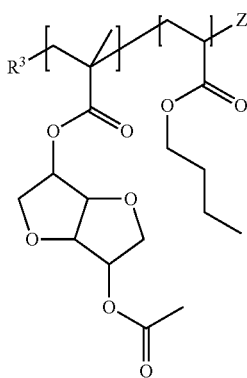

(XXXI)

where R$^3$ is as defined by structure (XXVIII) and Z is as defined by structure (XXIX).

The resulting dianhydrohexitol-based block copolymer, such as PAMI-b-PnBA, can have an improved thermal stability compared to the dianhydrohexitol-based CTA polymer or the conventionally free radical polymerized dianhydrohexitol-based polymer (e.g., PAMI). For example, PAMI-b-PnBA showed a marked increase in 7 compared to PAMI-CTA, e.g., for a $T_d$ defined by 5% weight loss in $N_2$ of about 216° C. and in air of about 296° C. Without being bound by any theory, it is believed that the higher $T_d$ of the dianhydrohexitol-based block copolymer (e.g., PAMI-b-PnBA) compared to the conventionally free radical polymerized dianhydrohexitol-based polymer (e.g., PAMI) is due to the differences in thermal stability and decomposition mechanisms between poly(acrylate)s and poly(methacrylate)s. For example, poly(acrylate)s tend to undergo thermal decomposition by a random-chain scission mechanism with a $T_d$ of about 310° C. while poly(methacrylate)s decompose by an end-chain mechanism at relatively lower temperatures. For example, for PAMI-CTA, methacrylic chain ends are likely generated by in situ thermolysis of the CTA end group during thermogravimetric analysis ("TGA"). Therefore, it is believed that the relatively higher thermal stability of PAMI-b-PnBA can be attributed to the absence of methacrylic chain ends.

The dianhydrohexitol-based block copolymer (e.g., PAMI-b-PnBA) can demonstrate two well-separated $T_g$ values. In some examples, the separate $T_g$ values are near the corresponding $T_g$ values of the respective homopolymers that make up the block copolymer, which suggests that the homopolymers (e.g., the PAMI and the PnBA) are microphase separated in the dianhydrohexitol-based block copolymer. For example, samples of PAMI-b-PnBA exhibited two well-separated $T_g$ values at about –45° C. and about 120° C., which is close to the respective $T_g$ for PnBA and PAMI, respectively. Microphase separation can be important for thermoplastic elastomer applications.

The PAMI-b-PnBA block copolymer described above is a diblock copolymer, i.e., a block copolymer comprising two primary block monomers. Similar techniques can be used to form triblock copolymers or multiblock copolymers of the dianhydrohexitol-based monomer of structure (I). For example, a triblock copolymer can be formed from PAAI as the outside blocks. PnBA from n-butyl acrylate of structure (XXX) as the basis of a low-$T_g$ midblock, with BTCBA of structure (XXVI) performing as a CTA between the outside PAAI blocks and the inside PnBA-based midblock. The triblock copolymer can be formed by first polymerizing n-butyl acrylate by reacting the n-butyl acrylate with BTCBA of structure (XXVI) in the presence of a free-radical initiator, such as AIBN, to form a midblock having the structure (XXXII):

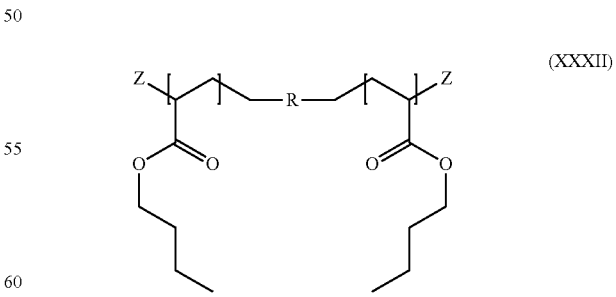

(XXXII)

wherein the R in the structure (XXXII) corresponds to the inner group of BTCBA (labeled as "R" in structure (XXXIII) below) and the Z in the structure (XXXII) corresponds to the outer groups of BTCBA (labeled as "Z" in structure (XXXIII) below):

(XXXIII)

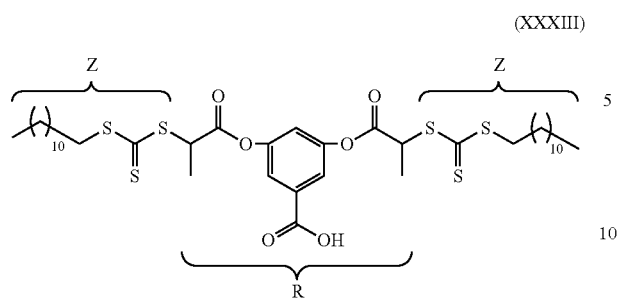

(XLI)

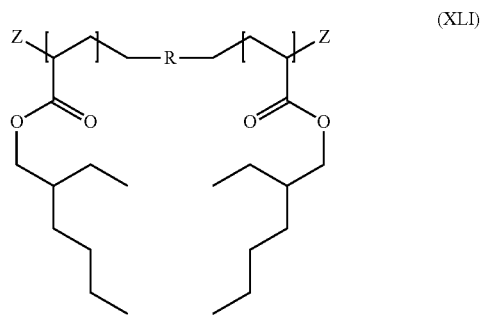

Next, AAI of structure (XVIII) is polymerized by RAFT polymerization by reacting the midblock of structure (XXXII) with AAI in a solvent, such as dimethylformamide ("DMF"), and with a free-radical initiator, such as AIBN, to initiate polymerization of the AAI to form outside PAAI blocks, e.g., one on either side of the midblock of structure (XXXII). The result of the RAFT polymerization of AAI with the midblock of structure (XXXII) is a polyacetylated acrylic isosorbide-block-poly-n-butyl acrylate-block-poly-acetylated acrylic isosorbide, referred to herein as "PAAI-b-PnBA-b-PAAI," having the structure (XXXIX).

wherein the R and Z in the structure (XLI) is defined in the same way as they were for the structure (XXXII).

Next, AAI of structure (XVIII) is polymerized by RAFT polymerization by reacting the midblock of structure (XLI) with AAI in a solvent, such as dimethylformamide ("DMF"), and with a free-radical initiator, such as AIBN, to initiate polymerization of the AAI to form outside PAAI blocks, e.g., one on either side of the midblock of structure (XLI). The result of the RAFT polymerization of AAI with the midblock of structure (XLI) is a polyacetylated acrylic isosorbide-block-poly-2-ethylhexyl acrylate-block-poly-acetylated acrylic isosorbide, referred to herein as "PAAI-b-PEHA-b-PAAI," having the structure (XLII).

(XXXIX)

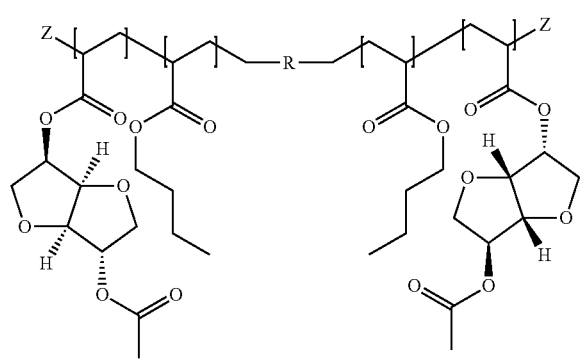

(XLII)

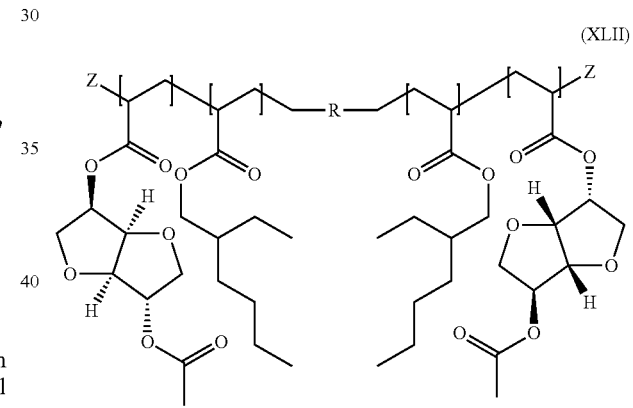

A similar example triblock copolymer can be formed with PAAI blocks and a low-$T_g$ midblock based on 2-ethylhexyl acrylate (EHA), which has the structure (XL), (XL)

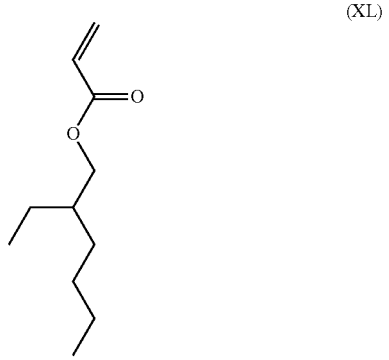

Much like the formation of the PAAI-b-PnBA-b-PAAI of structure (XXXIX), the EHA of structure (XL) is polymerized by reacting the EHA with BTCBA of structure (XXVI) in the presence of a free-radical initiator, such as AIBN, to form a midblock having the structure (XLI):

The PAAI-based triblock polymers described above, e.g., PAAI-b-PnBA-b-PAAI of structure (XXXIX) and PAAI-b-PEHA-b-PAAI of structure (XLII), are poly-AAI block copolymers with low-$T_g$ midblocks (e.g., the PnBA and PEHA midblocks) that can be formed relatively easily by RAFT polymerization. It has been found by the inventors that AAI more easily forms triblock polymers with low-$T_g$ midblocks such as those of structures (XXXIX) and (XLII) compared to AMI. It has also been discovered that PAAI formed by free-radical polymerization, e.g., the PAAI of structure (XXIV), can be formed in a substantially faster reaction time (as little as about 2 hours) compared to the formation of PAMI, e.g., the PAMI of structure (XXIII) by free-radical polymerization (about 18 hours).

EXAMPLES

Various embodiments of the present invention can be better understood by reference to the following Examples which are offered by way of illustration. The present invention is not limited to the Examples given herein.

Example 1

Synthesis of Acetylated Methacrylic Isosorbide (AMI) Monomer

AMI was prepared in two steps according to the reaction scheme shown in FIG. 1. In both steps scandium (III) triflate (Sc(OTf)$_3$) was used to catalyze the esterification of isosorbide with the corresponding anhydride. Compared to alternative Lewis acid catalysts, Sc(OTf)$_3$ and other lanthanide triflates were found to have unusual stability towards air and water. As a result, they can be handled under ambient atmosphere, do not require anhydrous reaction conditions, and can be easily recycled and reused without loss of activity.

Figure 2:
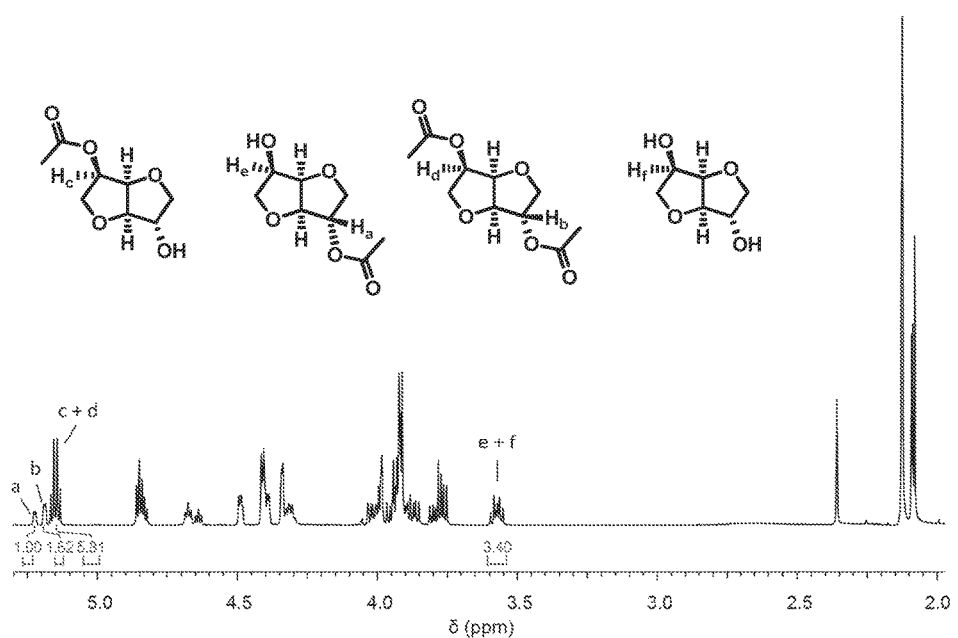
FIG. 2 shows a hydrogen-1 nuclear magnetic resonance (¹H NMR) spectrum of crude product mixture of Sc(OTf)₃ catalyzed acetylation of isosorbide with acetic anhydride.

In the first step of AMI synthesis (step a in FIG. 1), Sc(OTf)$_3$ was found to be an exceptionally active catalyst. Full consumption of acetic anhydride (1 mol eq.) occurred in less than 10 min at room temperature using a catalyst loading of 0.05 mol %. By comparison, reported reaction times for acetylation with acetic anhydride and 2 mol % lead (II) oxide range from 2-20 h. Analysis of the crude product mixture by $^1$H NMR spectroscopy indicated that the endo hydroxyl was the preferred site for acetylation ([endo-acetate]:[exo-acetate]=4.2:1.0; See FIG. 2).

After isolating the monoacetylated isosorbide products by column chromatography (54% yield), Sc(OTf)$_3$ was again used as a catalyst in the second step to install the methacrylate moiety (Step b in FIG. 1). Complete conversion of methacrylic anhydride (0.97 mol eq.) was reached after 4 h at 1 mol % catalyst loading. The reduced reactivity relative to the first step is attributed to the difference in sterics between acetic anhydride and methacrylic anhydride. Additionally, the majority of hydroxyl groups available for functionalization in the second step are located in the less active (but more sterically accessible) exo position.

Figure 3:
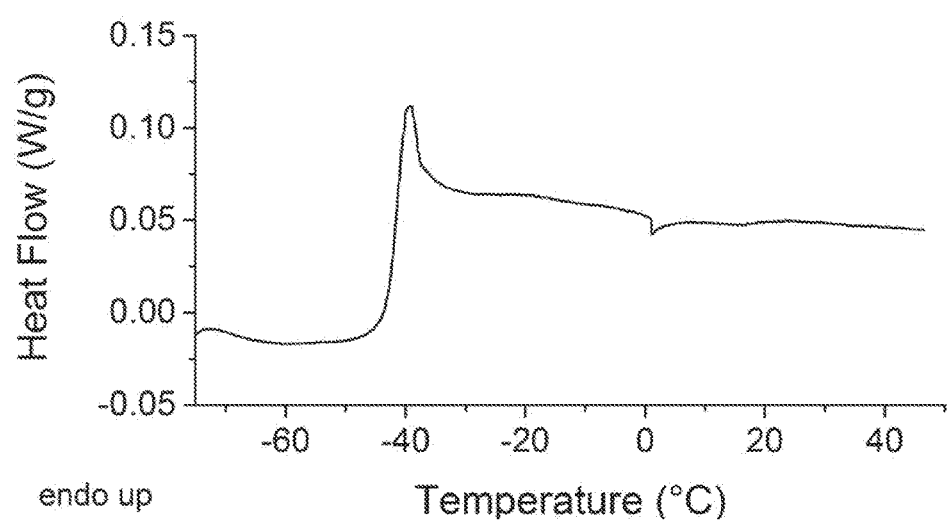
FIG. 3 is a graph of differential scanning calorimetry (DSC) of A-exo-MI in $N_2$, second heating at a heating rate of 10° C. min⁻¹.
Figure 4:
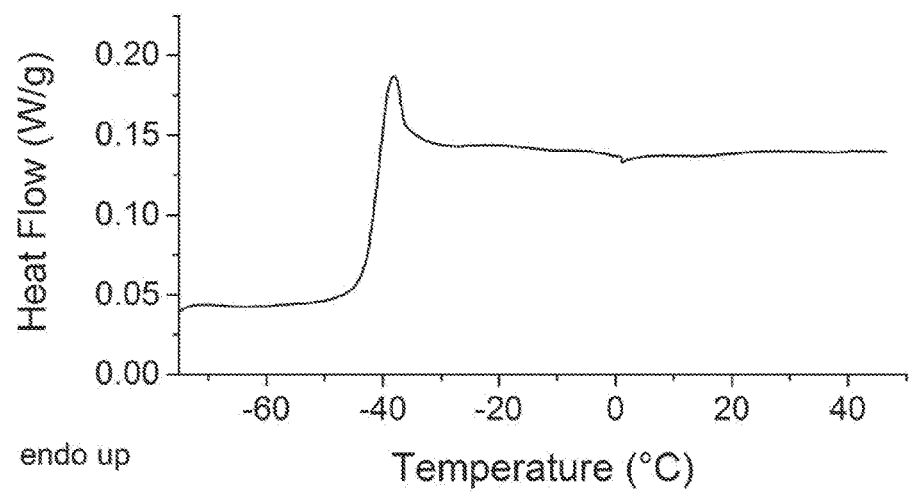
FIG. 4 is a graph of DSC of A-endo-MI in $N_2$, second heating, at a heating rate of 10° C. min⁻¹.
Figure 5:
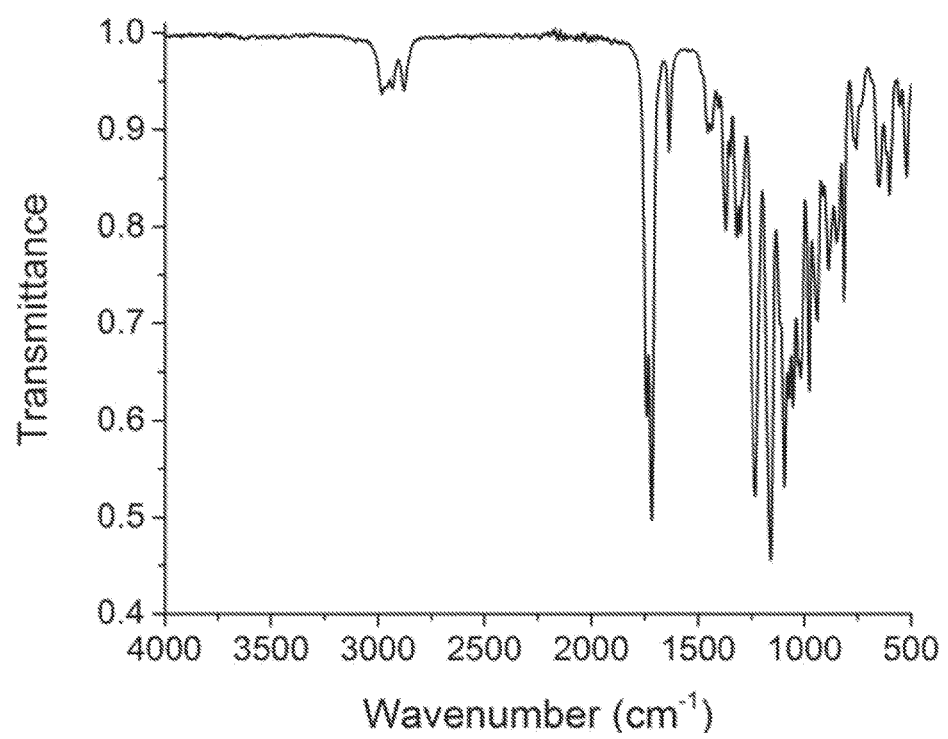
FIG. 5 is a graph of attenuated total reflect-Fourier transform infrared spectroscopy (ATR-FTIR) scan of neat A-exo-MI.
Figure 6:
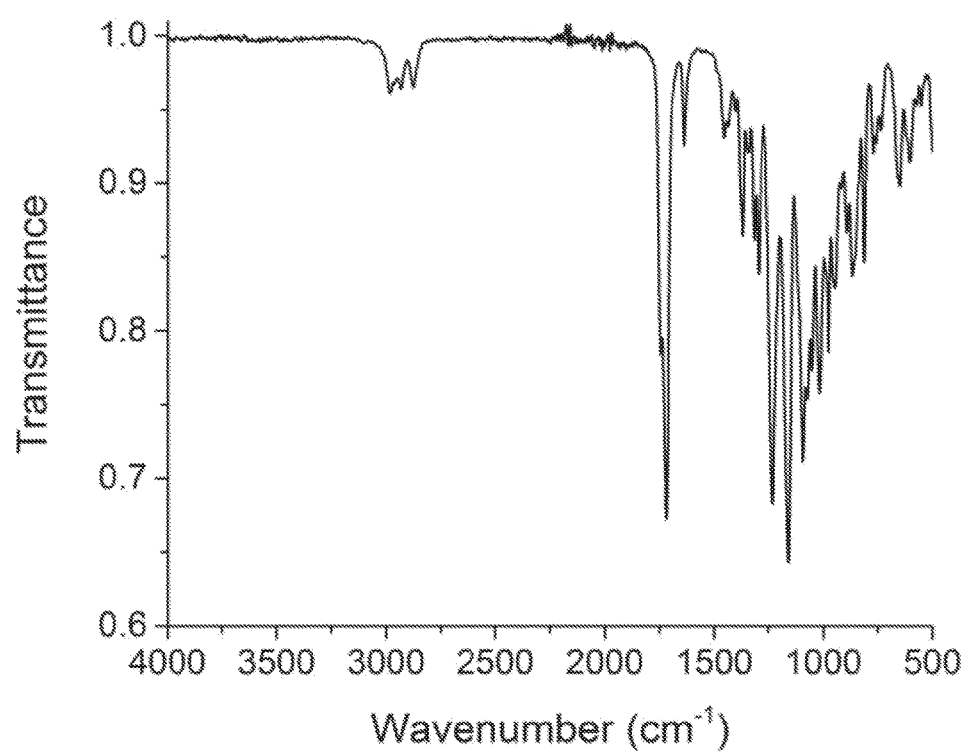
FIG. 6 is a graph of an ATR-FTIR scan of neat A-endo-MI.
Figure 7A:
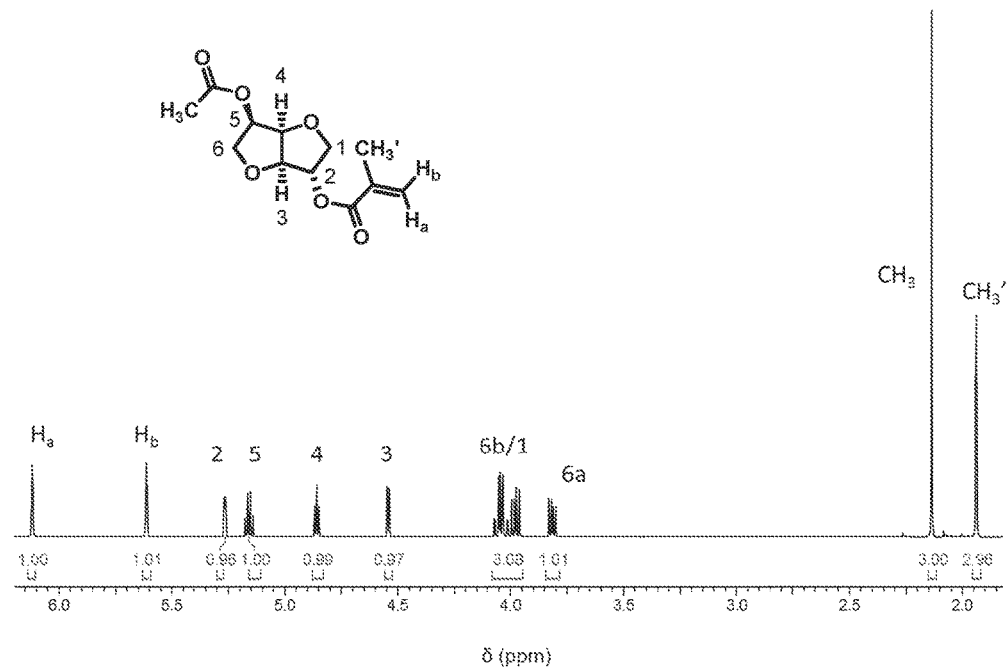
FIG. 7A shows an ¹H NMR spectrum of A-exo-MI in deuterated chloroform (CDCl₃).
Figure 7B:
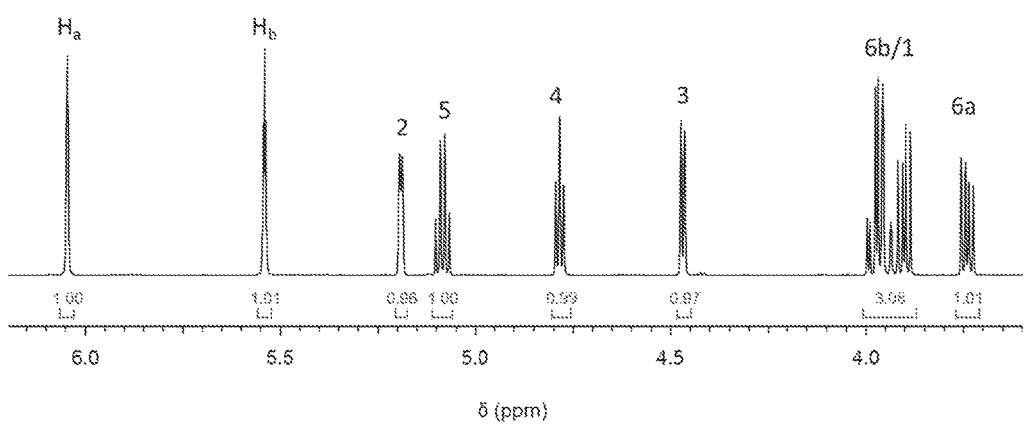
FIG. 7B shows an expanded view of the ¹H NMR spectrum of A-exo-MI in CDCl₃.
Figure 8A:
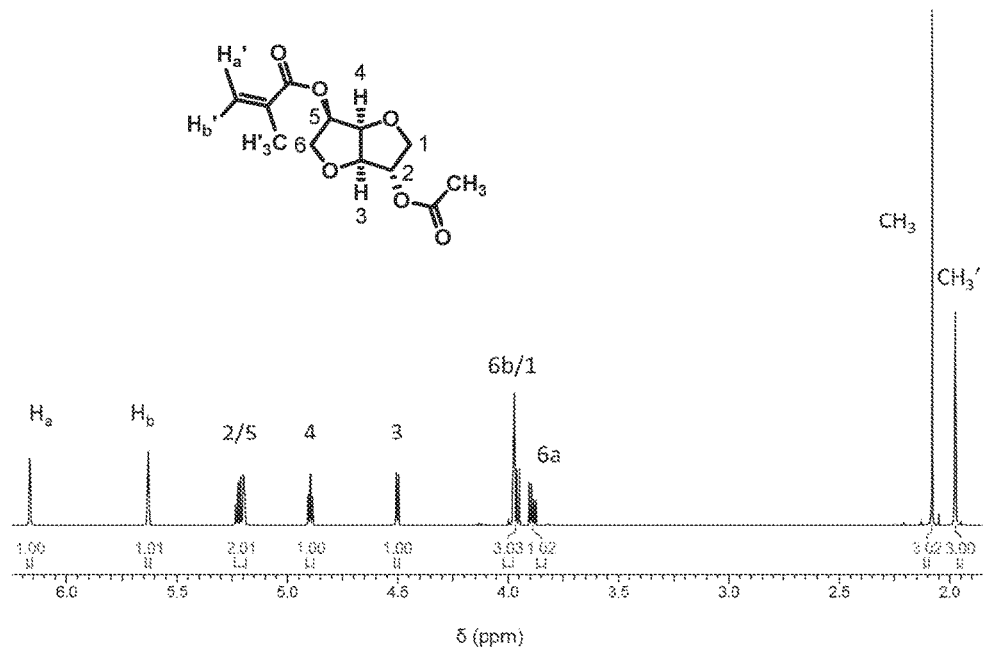
FIG. 8A shows an ¹H NMR spectrum of A-endo-MI in CDCl₃.
Figure 8B:
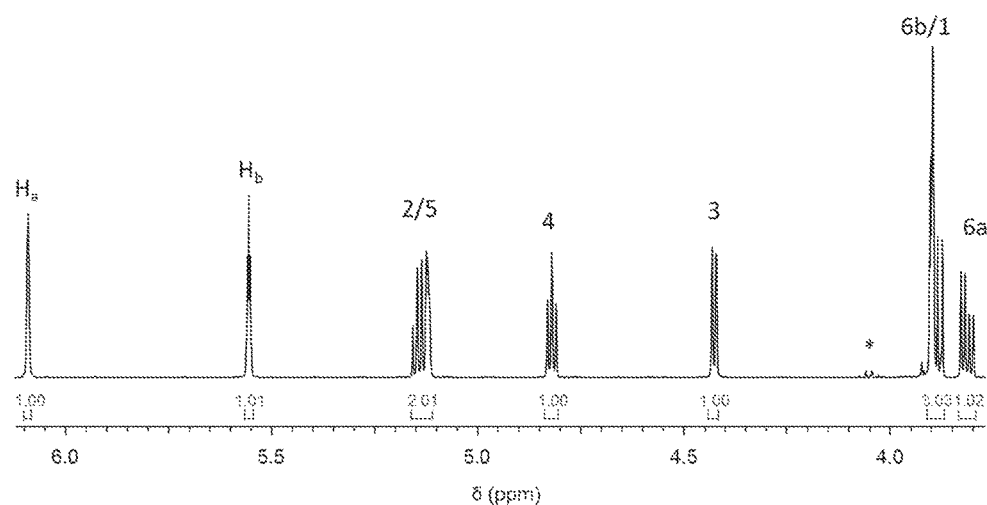
FIG. 8B shows an expanded view of the ¹H NMR spectrum of A-endo-MI in CDCl₃.
Figure 9:
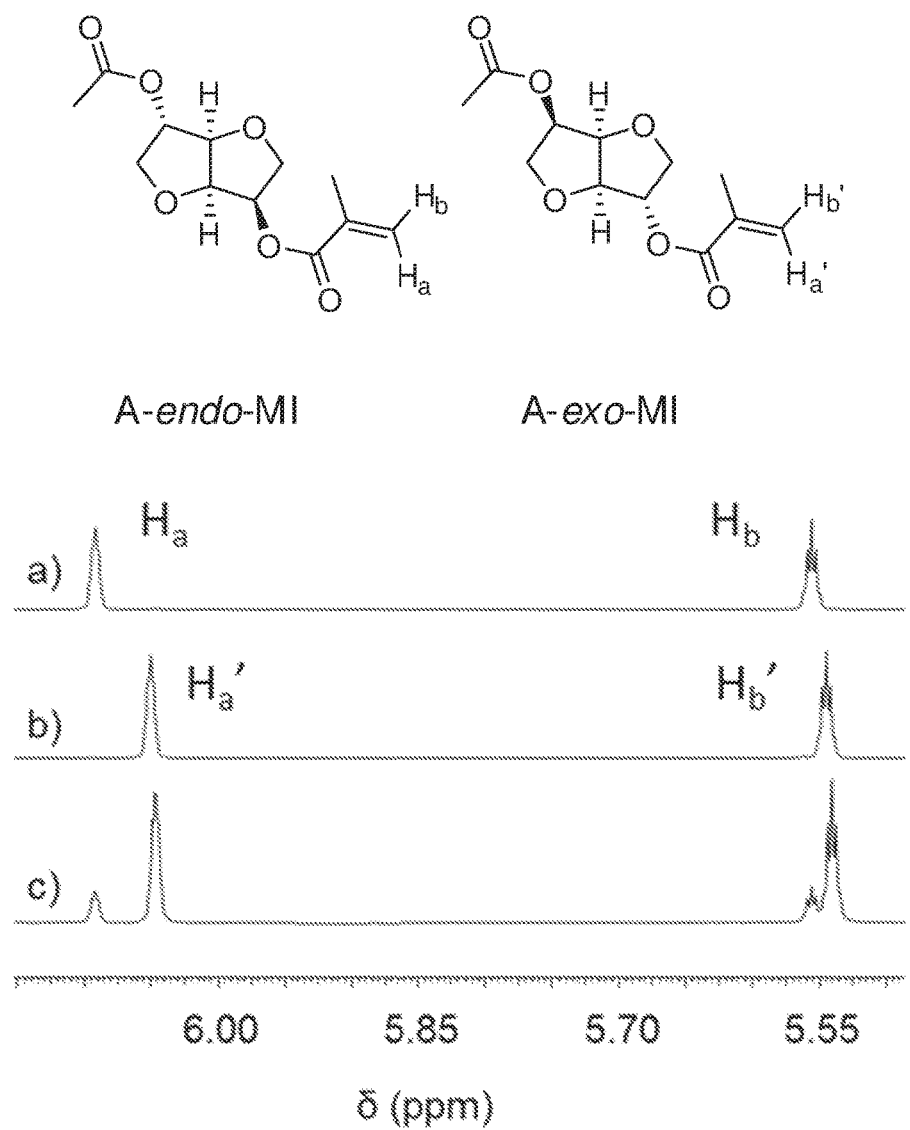
FIG. 9 shows an ¹H NMR spectra in CDCl₃ of the vinyl region for a) A-endo-MI, b) A-exo-MI, and c) a 4:1 mixture of A-exo-MI:A-endo-MI.

To characterize each isomer individually, pure samples of A-exo-MI and A-endo-MI were prepared by isolating select fractions from column chromatography of the first step containing only isosorbide endo-acetate or isosorbide exo-acetate, respectively, before installing the methacrylate moiety. Both A-exo-MI and A-endo-MI were clear viscous liquids at room temperature. Differential scanning calorimetry (DSC) showed identical $T_g$ values for the monomers A-exo-MI and A-endo-MI at $-42°$ C., and no evidence for crystallinity was observed for either isomer (see FIGS. 3 and 4). FT-IR spectroscopy showed characteristic peaks at 1740 and 1717 cm$^{-1}$ corresponding to the acyl and methacrylate esters, respectively, and the C=C bond stretch of the methacrylate group was apparent at 1637 cm$^{-1}$ (FIGS. 5 and 6). Other than subtle differences at low wavenumbers, no significant difference was observed in the FT-IR spectra for A-exo-MI and A-endo-MI. $^1$H NMR spectra differed significantly between A-exo-MI and A-endo-MI due to the different arrangement of substituents about the isosorbide core (FIGS. 7A, 7B, 8A, and 8B). Of particular note is the difference in chemical shift observed for the vinyl protons cis to the carbonyl oxygen (FIG. 9). Additional structural confirmation was provided by high resolution mass spectroscopy of the 4:1 mixture of A-exo-MI:A-endo-MI (expected: 256.2518; found: 279.0839 (M+Na$^+$); error 4.63 ppm). Overall AMI was readily prepared as a mixture of isomers in two steps from isosorbide on a ~20 g scale with a final (unoptimized) overall yield of 44%. The use of low catalyst loadings, mild reaction conditions, and inexpensive commercially available reagents make this synthetic pathway appealing for potential large scale production of the monomer.

Example 2

Free Radical Polymerization of AMI Monomer

Figure 10:
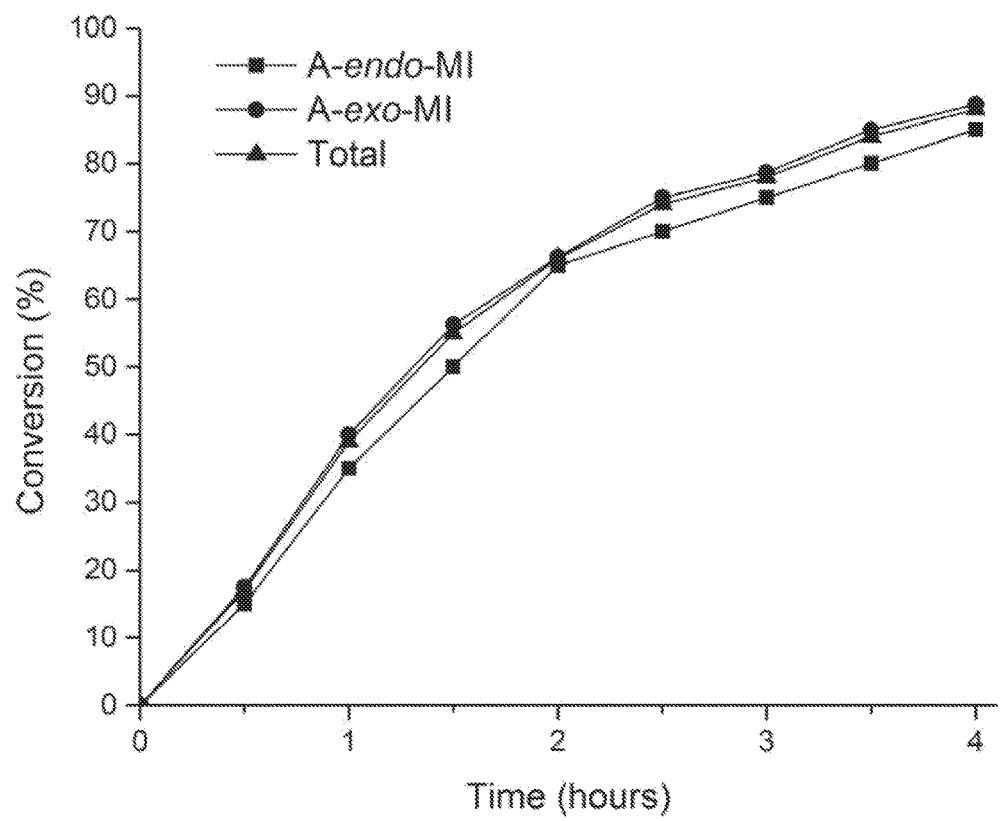
FIG. 10 is a graph of an example conversion over time for the free radical polymerization of AMI in chloroform (CHCl₃).
Figure 11:
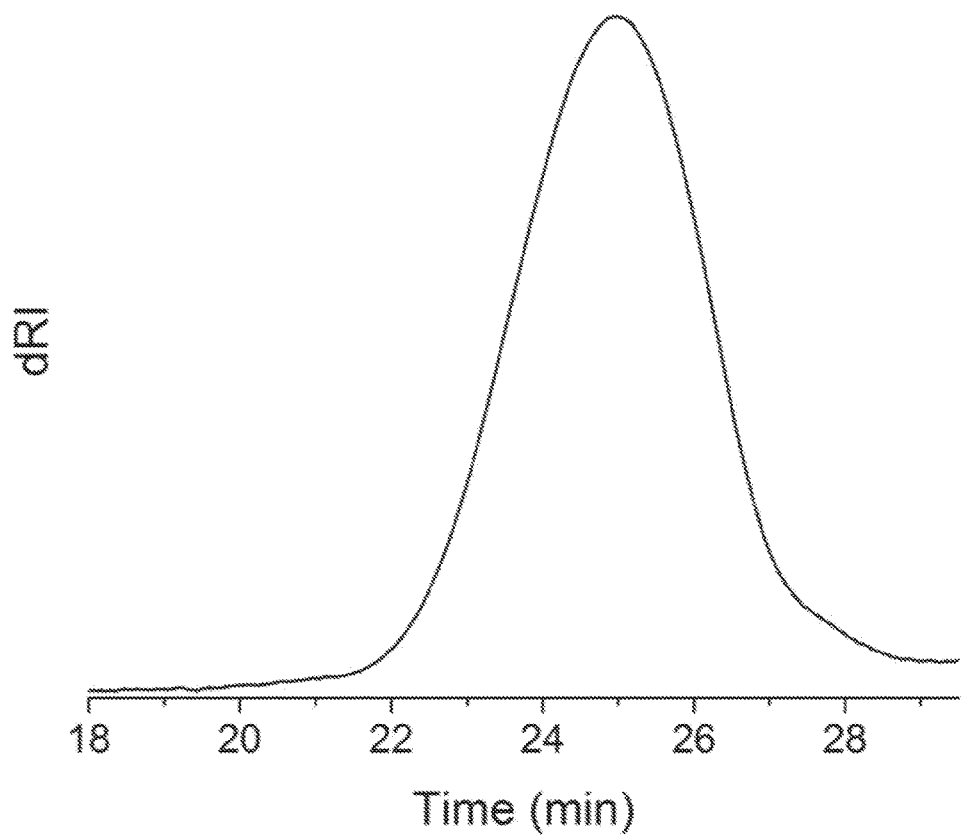
FIG. 11 is a graph of a run of size-exclusion chromatography in tetrahydrofuran (THF-SEC) of poly-acetylated methacrylic isosorbide (PAMI) prepared by free-radical polymerization with AIBN.
Figure 12:
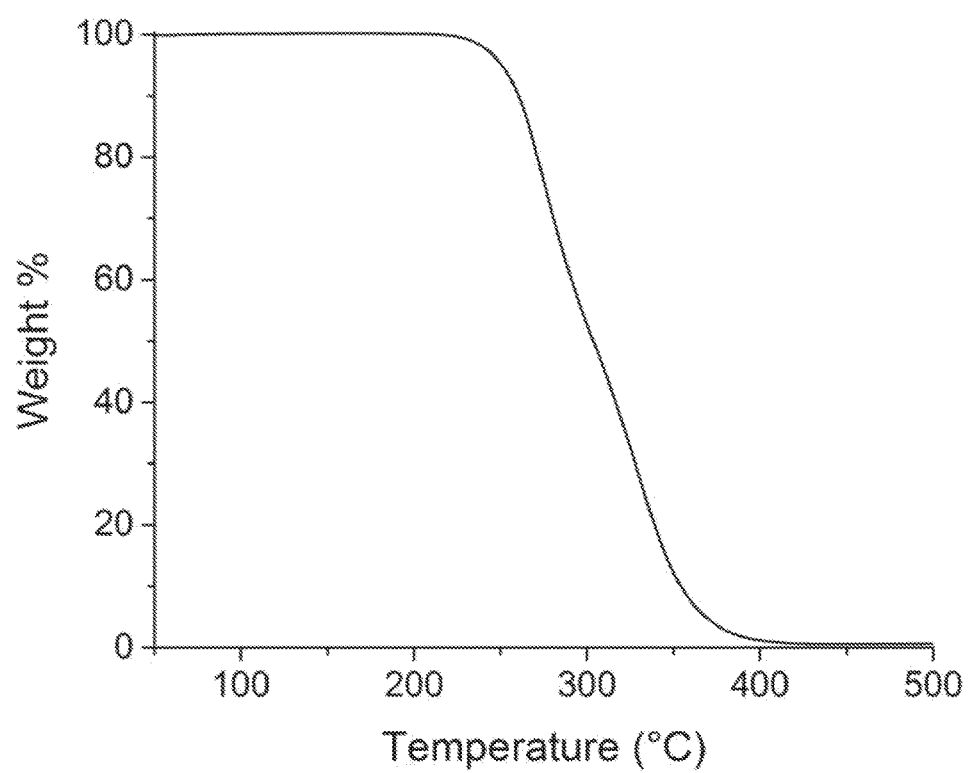
FIG. 12 is a graph of thermogravimetric analysis (TGA) in $N_2$ of PAMI prepared by free radical polymerization at a heating rate of 10° C. min⁻¹.
Figure 13:
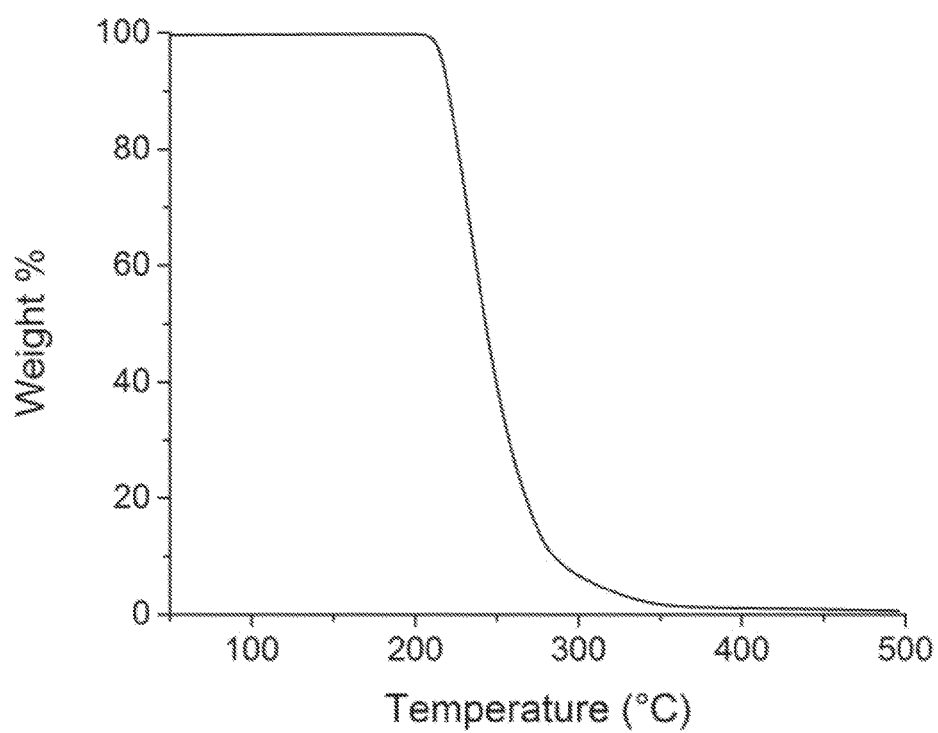
FIG. 13 is a graph of TGA in air of PAMI prepared by free radical polymerization at a heating rate of 10° C. min⁻¹.
Figure 14:
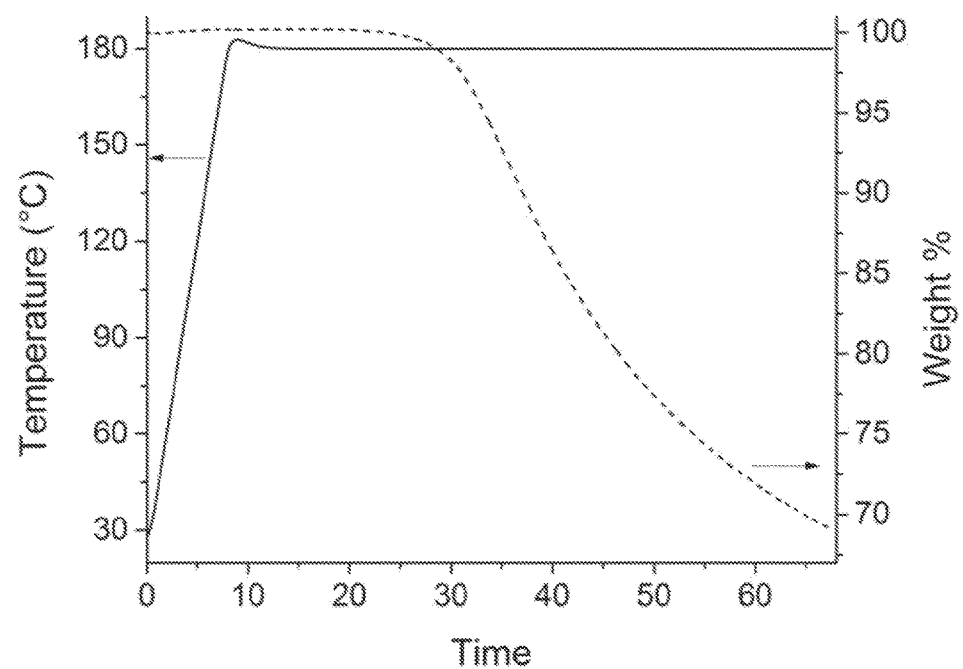
FIG. 14 is a graph of TGA in air at 180° C. of PAMI (number average molar mass ($M_n$) of 88.9 kg mol⁻¹) prepared by free radical polymerization.
Figure 15:
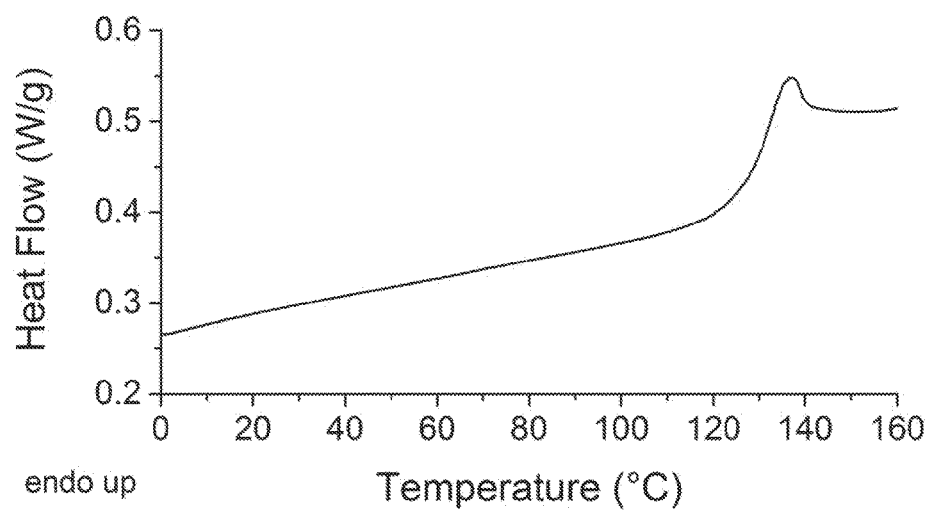
FIG. 15 is a graph of DSC of PAMI ($M_n$ of 88.9 kg mol⁻¹) in $N_2$, second heating, at a heating rate of 10° C. min⁻¹.

Thermally initiated free radical polymerization of AMI (4:1 A-exo-MI:A-endo-MI) was carried out in the presence of azobisisobutyronitrile (AIBN) at 70° C. in CHCl$_3$. Aliquots taken during the polymerization were analyzed by $^1$H NMR spectroscopy to determine conversion as a function of time (FIG. 10). $^1$H NMR analysis indicated 83% monomer conversion after 4 h. Monitoring the relative integrations of resonances corresponding to H$_a$ and H$_a$' (FIG. 9) indicated no significant difference in reactivity between A-endo-MI and A-exo-MI. After precipitation and drying, this sample of PAMI was soluble at 10 wt. % in acetone, EtOAc, CH$_2$Cl$_2$, CHCl$_3$, THF, and DMF but was insoluble in water, MeOH, iPrOH, and toluene. The number average molar mass (M$_n$) of this sample by size exclusion chromatography in THF with multi-angle laser light scattering detection (SEC-MALLS) was 88.9 kg mol$^{-1}$ with $Đ$=1.80 (FIG. 11). Thermogravimetric analysis (TGA) showed a T$_d$ (5% weight loss) of 251° C. and 217° C. under N$_2$ and air, respectively (FIGS. 12 and 13). Similar values of Td (~230° C.) under inert atmosphere have been reported previously for poly(methyl methacrylate) (PMMA) prepared by free radical polymerization. Under air this sample of PAMI was stable for ~20 minutes at 180° C. (<1% weight loss, FIG. 14). The sample exhibited a remarkably high T$_g$ of 130° C. by DSC (FIG. 15). Since the T$_g$ of PMMA is ~110° C., the relatively high T$_g$ of PAMI is attributed to reduced polymer flexibility caused by additional steric bulk of the pendant isosorbide acetate groups.

Figure 16:
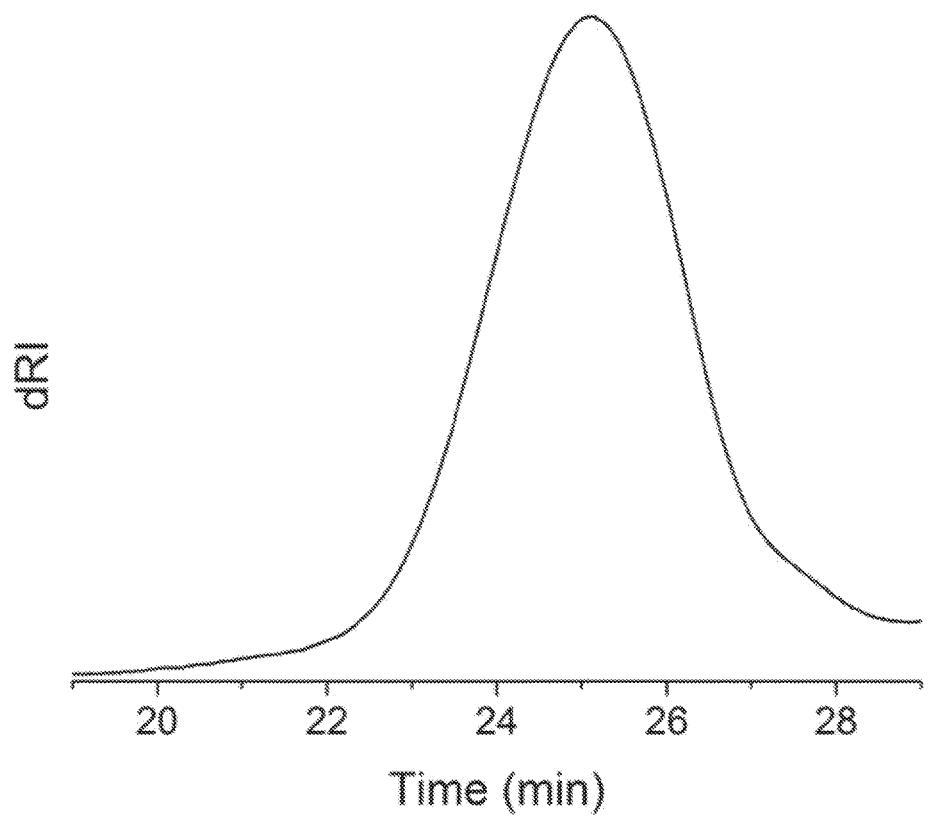
FIG. 16 is a graph of THF-SEC of PA-endo-MI ($M_n$ of 105 kg mol⁻¹).
Figure 17:
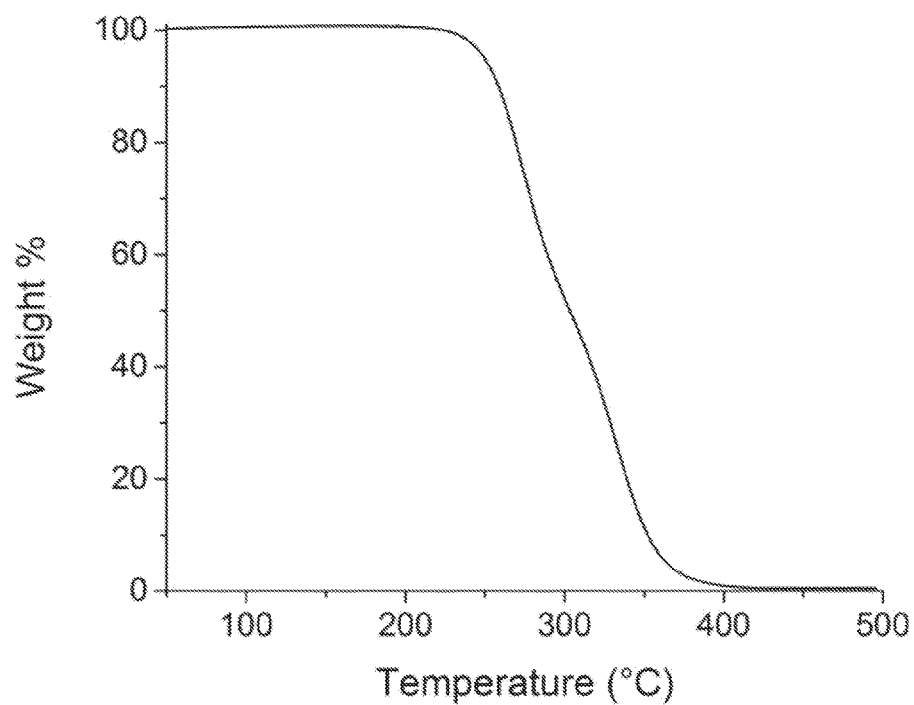
FIG. 17 is a graph of TGA in $N_2$ of PA-endo-MI at a heating rate of 10° C. min⁻¹.
Figure 18:
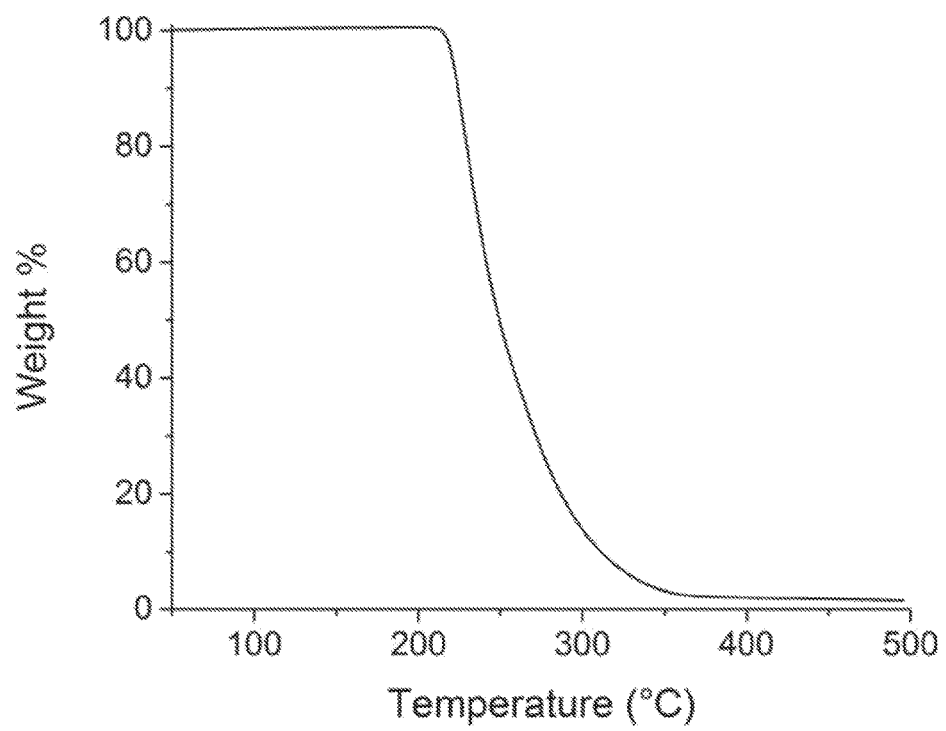
FIG. 18 is a graph of TGA in air of PA-endo-MI at a heating rate of 10° C. min⁻¹.
Figure 19:
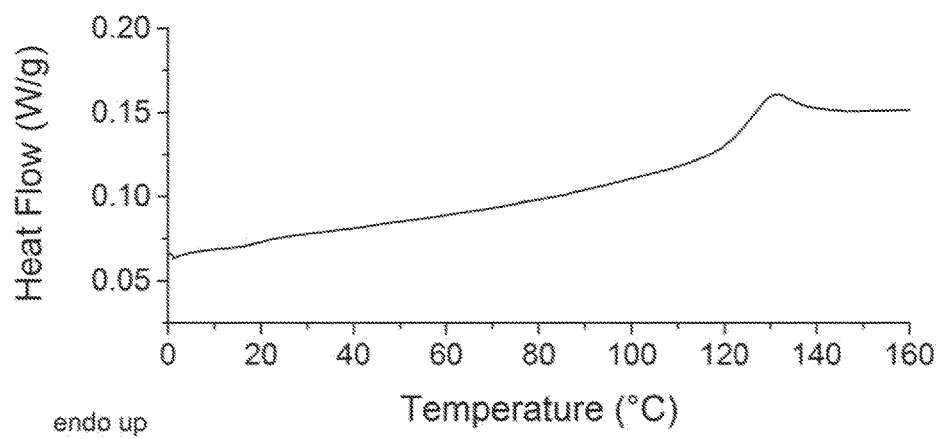
FIG. 19 is a graph of DSC of PA-endo-MI (105 kg mol⁻¹) in $N_2$, second heating, at a heating rate of 10° C. min⁻¹.

To determine the effect of stereochemistry on polymer thermal properties, an isomerically pure sample of PAMI was prepared from A-endo-MI under the same conditions described above. Similarly, after 4 h at 70° C. the polymerization of A-endo-MI reached 84% conversion as determined by $^1$H NMR spectroscopy. M$_n$ and $Đ$ of PA-endo-MI by SEC-MALLS analysis were 105 kg mol$^{-1}$ and 1.48, respectively (FIG. 16). TGA and DSC revealed no significant difference in T$_d$ or T$_g$ between PAMI and PA-endo-MI, indicating that the regiochemistry of substituents on isosorbide does not alter the thermal properties of PAMI (Table 1, FIGS. 17, 18, 19). Based on these results. AMI and PAMI can be prepared without the need for careful consideration of isomer composition in the final product.

TABLE 1

Comparison of molar mass and thermal properties of PAMI vs PA-endo-MI.

| Sample | AMI composition[a] | M$_n$ (kg mol$^{-1}$)[b] | $Đ$[b] | T$_d$ (N$_2$, air, ° C.)[c] | T$_g$ (° C.)[d] |
|---|---|---|---|---|---|
| PAMI | 4.0:1 | 88.9 | 1.80 | 251, 217 | 130 |
| PA-endo-MI | 0:1 | 105 | 1.48 | 250, 221 | 123 |

[a]Monomer feed ratio.
[b]Determined by SEC-MALLS in THF.
[c]From TGA.
[d]From DSC.

Example 3

Raft Polymerization of AMI Monomer

Figure 21:
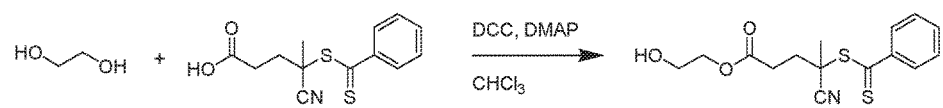
FIG. 21 is a flow diagram of an example reaction scheme for the synthesis of 4-cyano-4-(phenylcarbonothioylthio) pentanoate (HO-CPAD).
Figure 22:
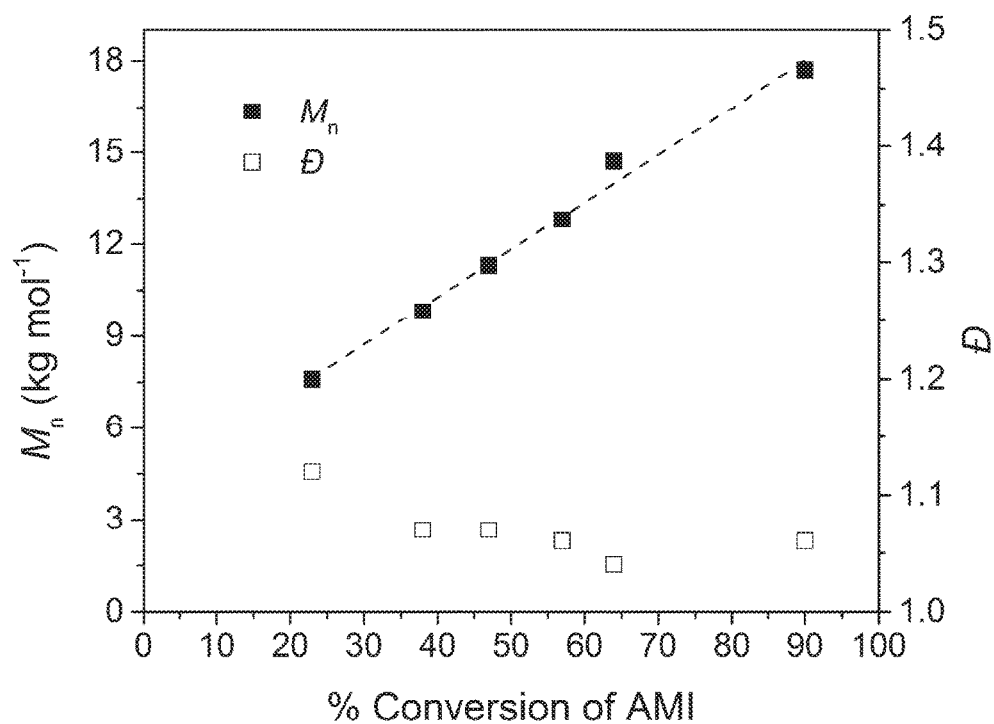
FIG. 22 is a graph of the number average molar mass ($M_n$) and the dispersity ($Đ$) as a function of conversion for RAFT polymerization of AMI. [AMI]:[HO-CPAD]:[AIBN]=60:1:0.1. Conversion determined by ¹H NMR spectroscopy. $M_n$ and $Đ$ determined by SEC-MALLS in THF. The dashed line indicates a linear regression, $R^2$=0.99.

Controlled radical polymerization allows for the synthesis of macromolecules with well-defined architectures. Block copolymers, which find use in many applications such as thermoplastic elastomers, pressure sensitive adhesives, and toughening agents, are readily prepared by controlled radical polymerization methods. The thermal stability and high $T_g$ of PAMI make it a promising sustainable candidate for a hard component of a block copolymer system. To demonstrate the ability to incorporate PAMI into a block copolymer, AMI was polymerized via RAFT to give PAMI-CTA (step a in FIG. 20). An initial screening showed that dithiobenzoates were the most suitable class of chain transfer agent (CTA) for RAFT polymerization of AMI, while trithiocarbonates did not result in well controlled polymerizations (Table 2). The CTA that afforded the highest monomer conversion while maintaining low $Đ$ of the resultant polymer was 4-cyano-4-(phenylcarbonothioylthio)pentanoate (HO-CPAD). This CTA is a structural analogue of 4-cyano-1-hydroxypent-4-yl dithiobenzoate, and was synthesized by Steglich esterification of the commercially available 4-cyano-4-(phenylcarbonothioylthio)pentanoic acid with excess ethylene glycol (shown in the reaction scheme of FIG. 21). After purification by column chromatography, HO-CPAD was isolated in a 67% yield. Use of HO-CPAD as a RAFT CTA results in functional polymers with a hydroxyl end group (FIG. 2), a particularly useful structural motif given the synthetic versatility of a hydroxyl group (e.g., in the preparation of block copolymers containing mechanistically differentiated components). A linear increase in $M_n$ with conversion and narrow molecular weight distribution indicated the RAFT polymerization of AMI with HO-CPAD was well controlled (FIG. 22). However, the linear fit to the $M_n$ vs. conversion data has a non-zero intercept. This phenomenon can be attributed to non-RAFT propagation events occurring at low conversion before the main RAFT equilibrium has been established.

TABLE 2

RAFT polymerization of AMI with different CTAs.

| CTA | Conversion (%) | $M_n$ (kg/mol) | $Đ$ |
|---|---|---|---|
| HO-CPAD | 92 | 30.9 | 1.08 |
| 1 | 57 | 20.7 | 1.08 |
| 2 | 61 | 30.0 | 1.11 |
| 3 | 69 | 20.2 | 1.10 |
| 4 | 77 | 46.4 | 1.80 |
| 5 | 22 | n.d. | n.d. |

[AMI]:[CTA]:[AIBN] = 100:1:0.1, 70° C., DMF, 18 h. Conversion from $^1$H NMR spectroscopy, $M_n$ and $Đ$ determined by SEC-MALS in THF.
n.d. = not determined.

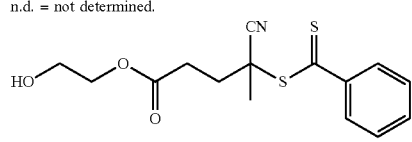

HO-CPAD

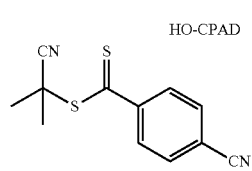

1

TABLE 2-continued

RAFT polymerization of AMI with different CTAs.

| CTA | Conversion (%) | $M_n$ (kg/mol) | $Đ$ |
|---|---|---|---|

2

3

4

5

Figure 23:
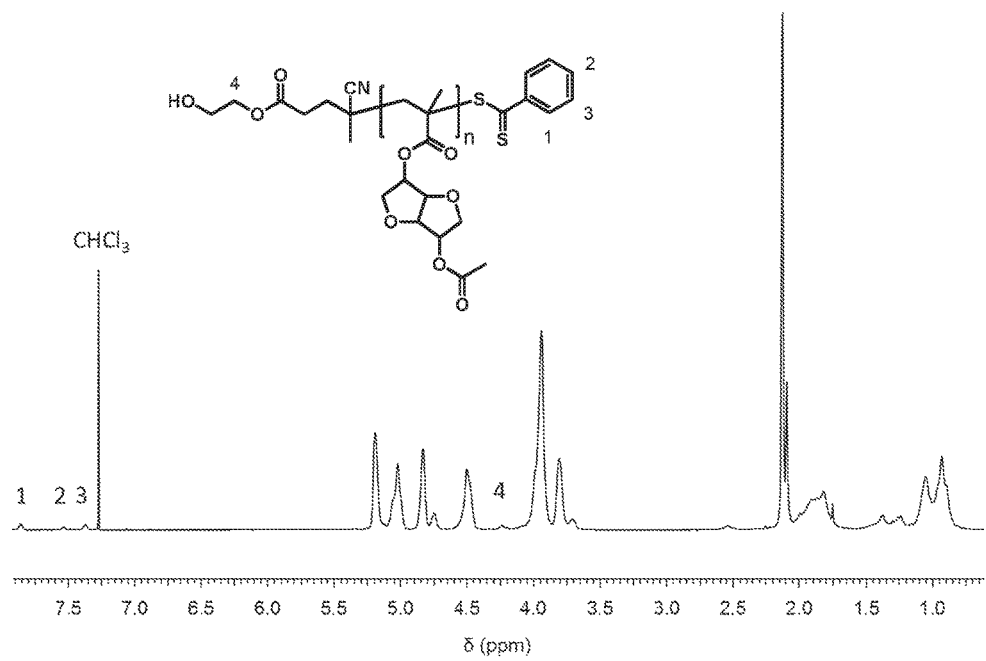
FIG. 23 is an ¹H NMR spectrum of PAMI-CTA sample 14 in CDCl₃.
Figure 24:
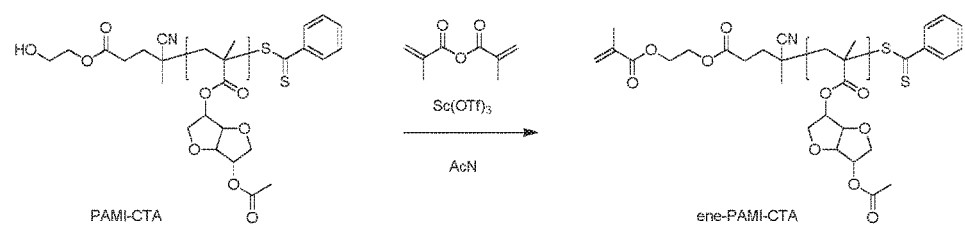
FIG. 24 is a flow diagram of an example reaction scheme for the synthesis of ene-PAMI-CTA. [PAMI-CTA]:[anhydride]:[Sc(OTf)₃]=1:10:0.14.
Figure 25:
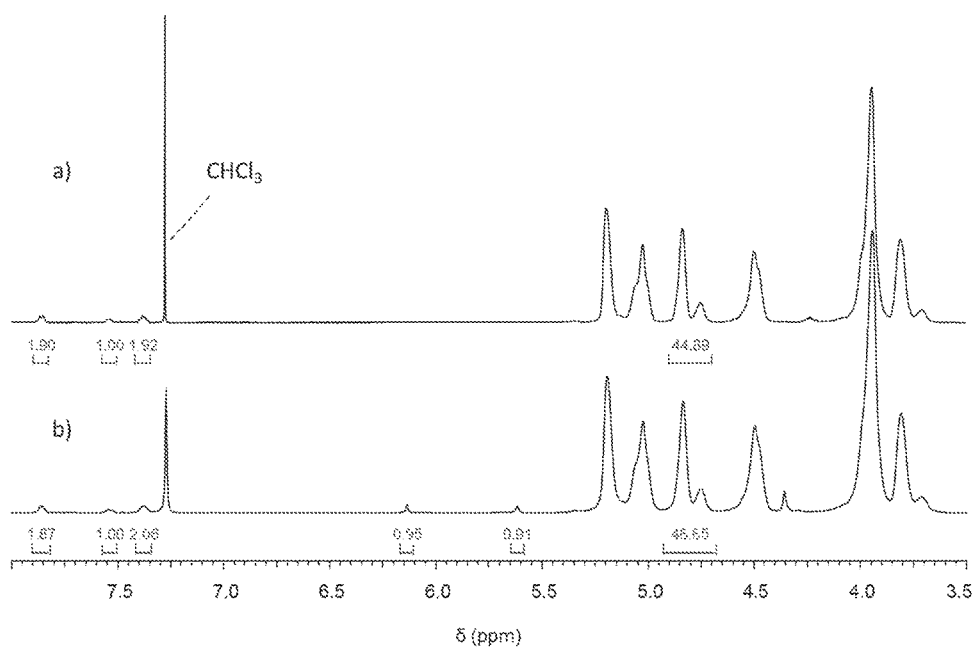
FIG. 25 show ¹H NMR spectrum analysis of a) PAMI-CTA sample 14 and b) ene-PAMI-CTA sample 14 in CHCl₃. Molar ratio based on integrations of end group CTA:end group$_{ene}$ for ene-PAMI-CTA sample 14=1:0.94. Integration ratio of aromatic protons of PAMI-CTA:ene-PAMI-CTA=1:0.98 (standardized to repeat unit integration).

Since a key advantage of controlled radical polymerization is the ability to synthesize materials with targeted molar masses and narrow distributions, AMI was polymerized by RAFT employing different ratios of [AMI]$_0$:[HO-CPAD]$_0$ (Table 3). In all cases the polymerization proceeded to >92% conversion after 18 h and $Đ$<1.09 was achieved for all samples. Analysis of PAMI-CTA (14) by $^1$H NMR spectroscopy confirmed the presence of the expected end groups (FIG. 23). Resonances between 7.36 and 7.89 ppm correspond to the aromatic protons of the dithiobenzoate group, while a peak at 4.23 ppm corresponds to the protons a to the alcohol of the free radical leaving group fragment. Further proof of a terminal hydroxyl group was demonstrated by reacting PAMI-CTA (14) with a tenfold excess of methacrylic anhydride in the presence of Sc(OTf)$_3$ (14 mol % relative to polymer) to give ene-PAMI-CTA (14) (shown in the reaction scheme of FIG. 24). Again. Sc(OTf)$_3$ was found to be an efficacious esterification catalyst. After 1 h of reaction at room temperature followed by repeated precipitation into MeOH and drying under vacuum, PAMI-CTA (14) was isolated as a pink powder. The disappearance of the peak at 4.23 ppm along with the appearance of a new peak at 4.36 ppm confirmed the terminal hydroxyl group was fully functionalized, while resonances corresponding to the methacrylic protons were observed in the vinyl region at 5.62 and 6.14 ppm (FIG. 25).

Values of $M_n$ as determined by $^1$H NMR end group analysis (assuming one CTA fragment per chain) and SEC-MALLS were in reasonably good agreement, although the values determined by SEC-MALLS were consistently higher (see Table 3). Values of $M_n$ (calc.)/$M_n$ (SEC-MALLS) was <1 for all trials, indicating a deviation from the ideal one CTA per chain model (e.g., CTA efficiency factor<1). For comparison, the $M_n$ (calc.)/$M_n$ (NMR) values were consistently closer to 1. Since conversion and $M_n$ (calc.)/$M_n$ (SEC-MALLS) and $M_n$ (calc.)/$M_n$ (NMR) were consistent across all trials, PAMI-CTA of a targeted $M_n$ can be reliably synthesized by RAFT using HO-CPAD.

Figure 26:
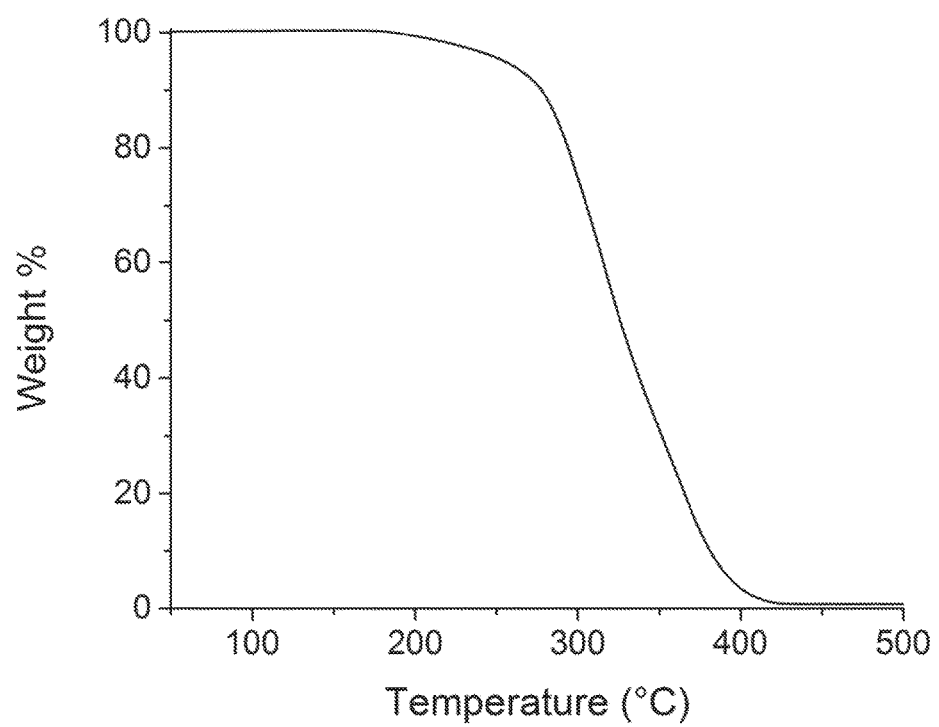
FIG. 26 is a graph of TGA in $N_2$ of PAMI-CTA sample 14 at a heating rate of 10° C. min⁻¹.
Figure 27:
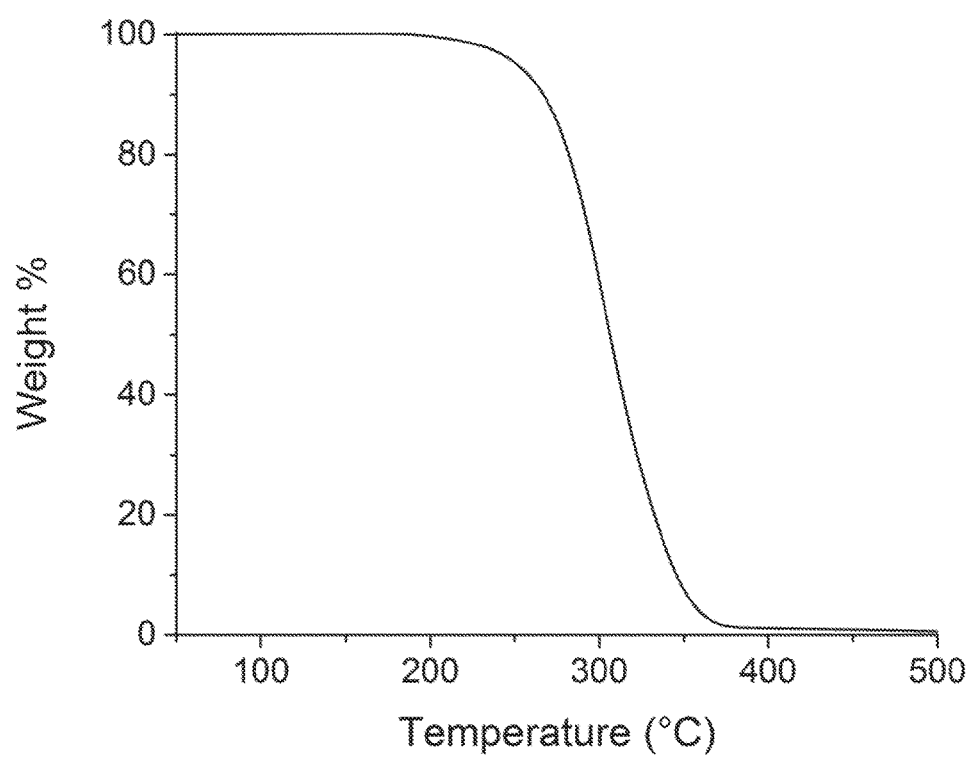
FIG. 27 is a graph of TGA in air of PAMI-CTA sample 14 at a heating rate of 10° C. min⁻¹.
Figure 28:
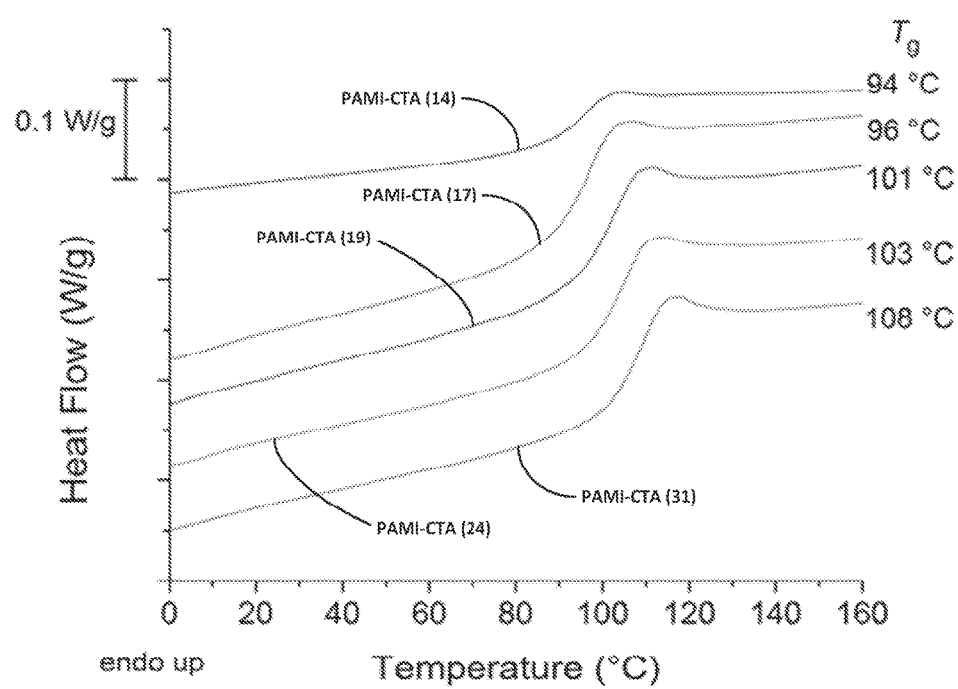
FIG. 28 is a graph of DSC of several samples of PAMI-CTA, second heating, at a heating rate of 10° C. min⁻¹.
Figure 29:
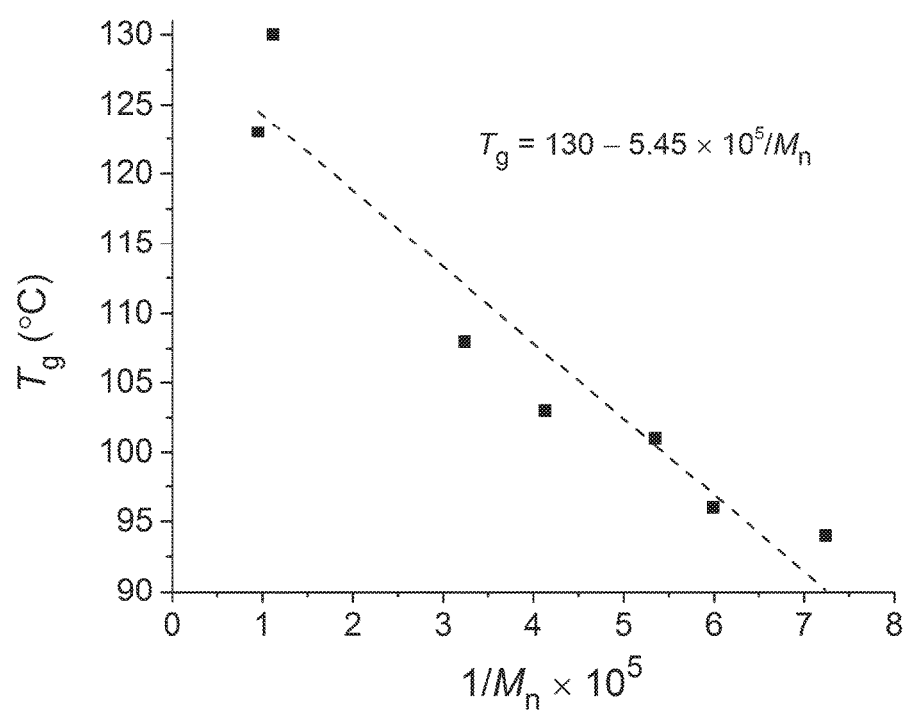
FIG. 29 is a plot of the glass transition temperature ($T_g$) vs. the inverse of the number average molar mass ($1/M_n$) for PAMI-CTA, PAMI, and PA-endo-MI. The dashed line is a linear regression of the form $T_g(M_n)=T_g(M_n\rightarrow\infty)-A/M_n$, where A is an empirical parameter. $R^2$=0.90.
Figure 30:
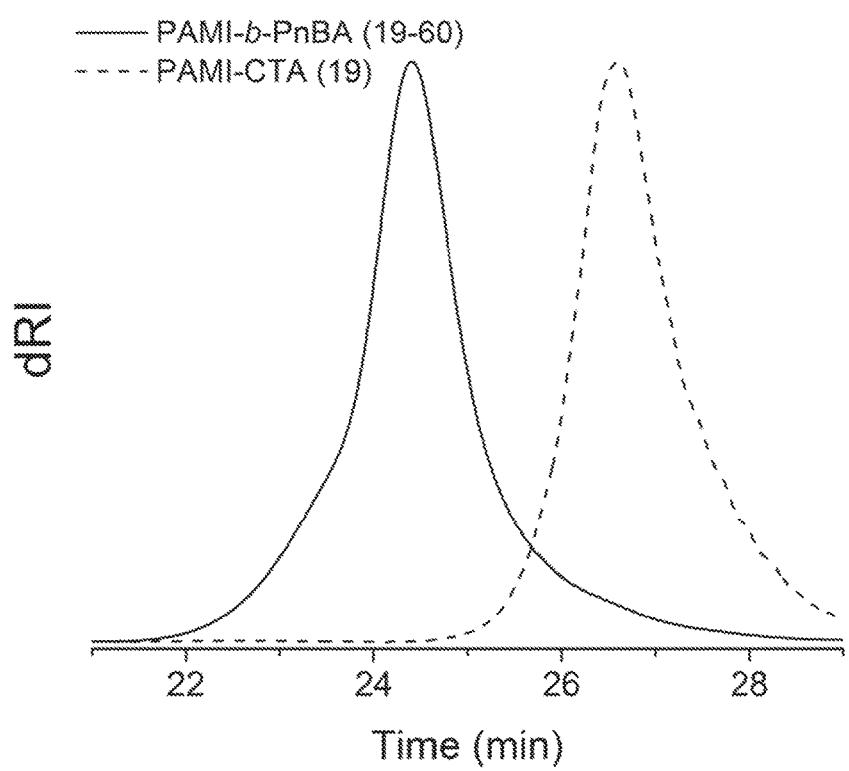
FIG. 30 is a graph of THF-SEC of PAMI-b-PnBA and PAMI-CTA sample 19 prepared by RAFT polymerization.
Figure 31:
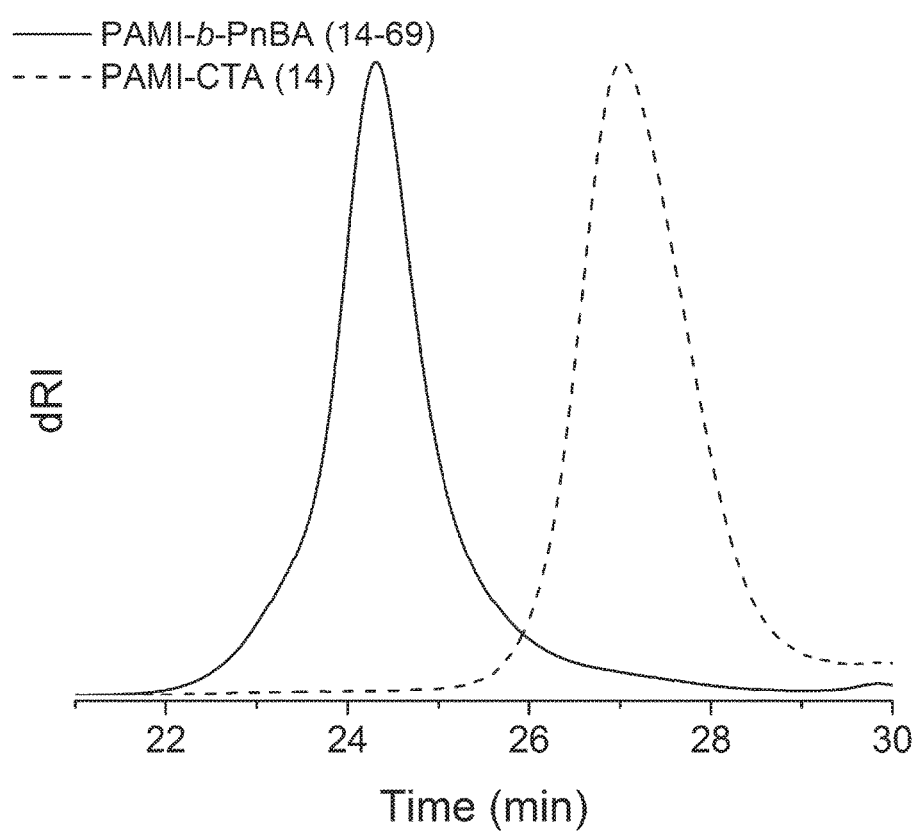
FIG. 31 is a graph of THF-SEC of PAMI-b-PnBA samples 14-69 prepared by RAFT.
Figure 32:
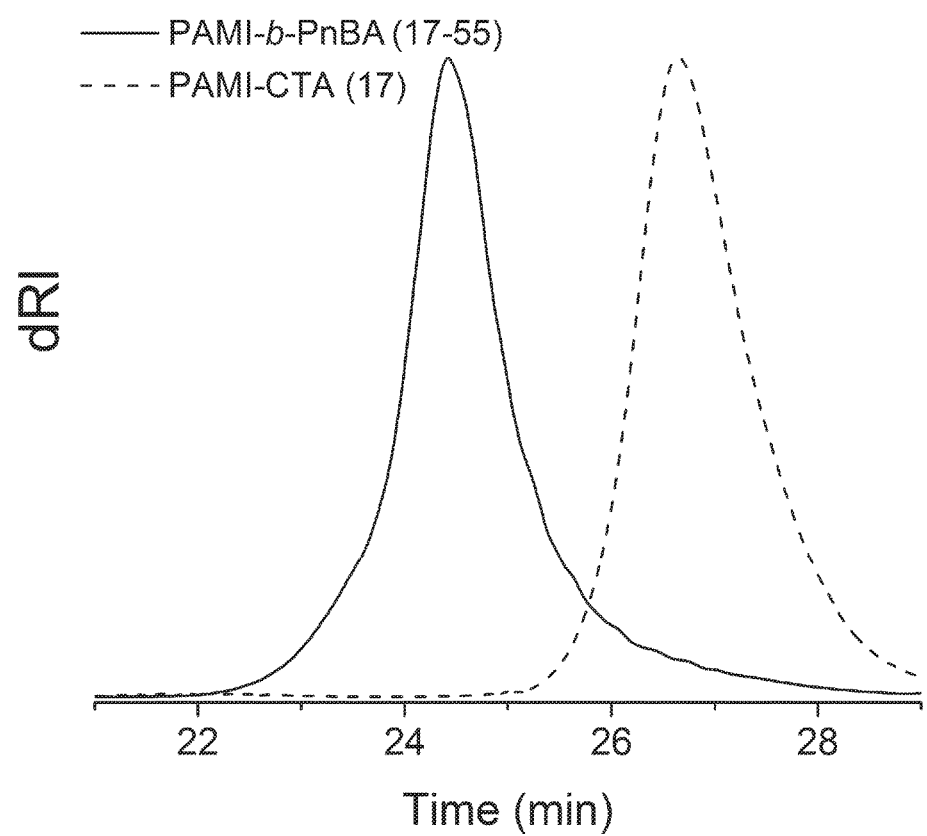
FIG. 32 is a graph of THF-SEC of PAMI-b-PnBA samples 17-55 prepared by RAFT.
Figure 33:
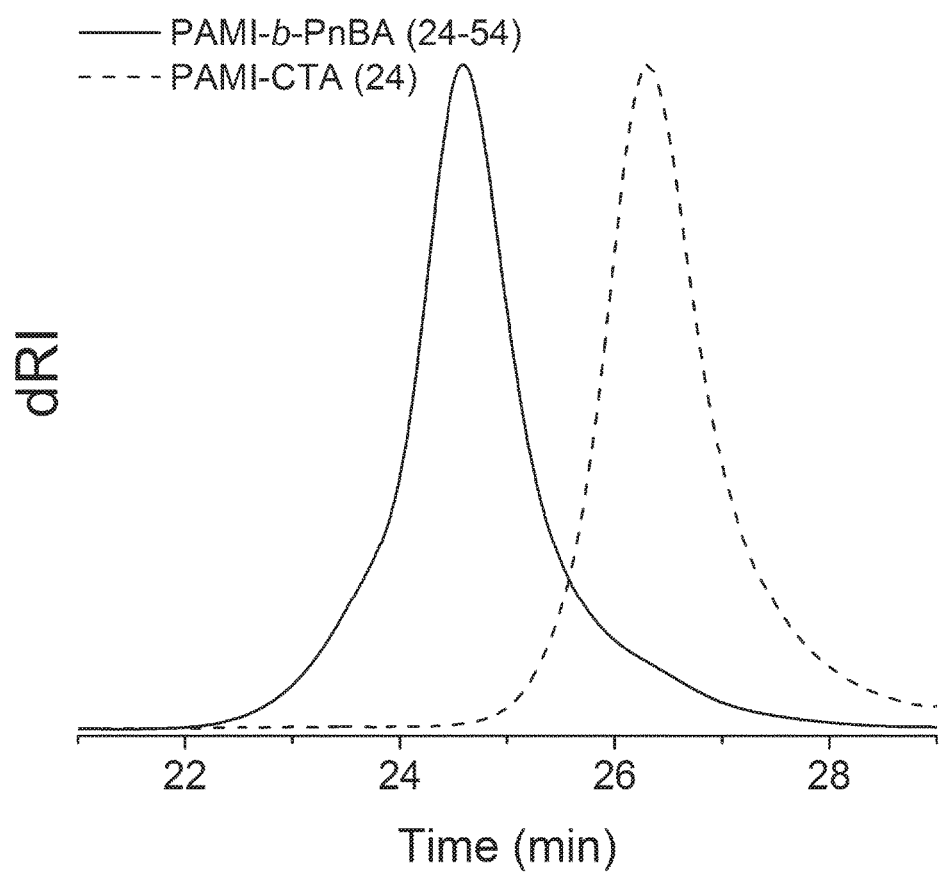
FIG. 33 is a graph of THF-SEC of PAMI-b-PnBA samples 24-54 prepared by RAFT.
Figure 34:
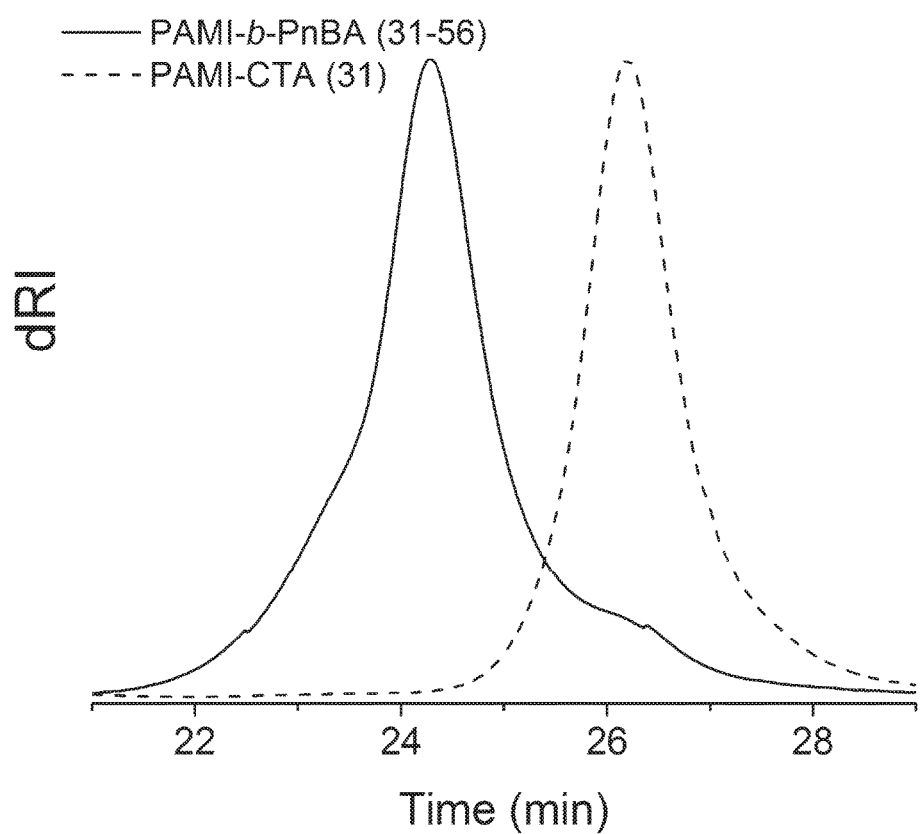
FIG. 34 is a graph THF-SEC of PAMI-b-PnBA samples 31-56 prepared by RAFT.
Figure 37:
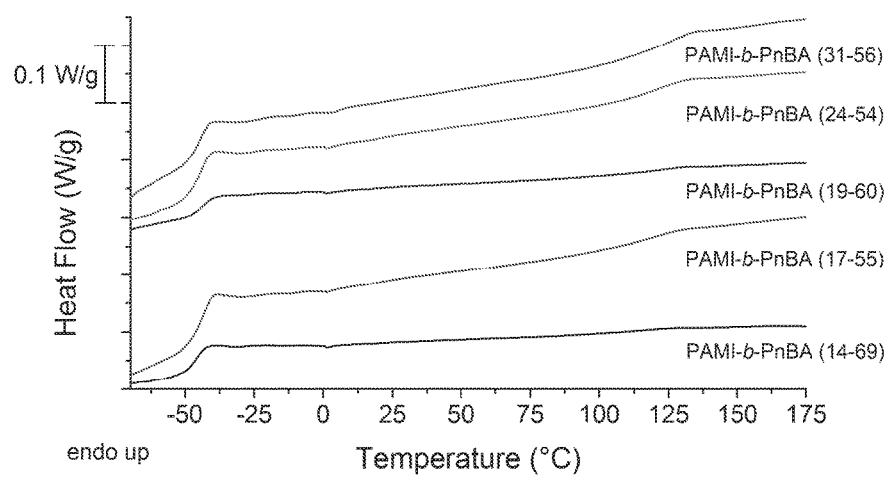
FIG. 37 is a graph of DSC of several samples of PAMI-b-PnBA in $N_2$, second heating, at a heating rate of 10° C. $min^{-1}$.

PAMI-CTA (14) exhibited similar thermal stability under $N_2$ and air ($T_d$=255 and 252° C., respectively, FIGS. 26 and 27). $T_g$ values of PAMI-CTA ranged from 91-108° C. depending on $M_n$ of the sample (FIG. 28). From the linear regression of $T_g$ vs. $1/M_n$ data based on the Flory-Fox equation, $T_g$ becomes essentially constant at 130° C. for PAMI at molar masses >55 kg mol$^{-1}$ (FIG. 29). These predicted values are in good agreement with the $T_g$ values observed for PAMI and PA-endo-MI prepared by conventional free radical polymerization.

pose by an end-chain mechanism at relatively lower temperatures. For PAMI-CTA, methacrylic chain ends are likely generated by in situ thermolysis of the CTA end group during TGA. Therefore, the relatively higher thermal stability of PAMI-b-PnBA is attributed to the absence of methacrylic chain ends. All samples of PAMI-b-PnBA exhibited two well-separated $T_g$ values at approximately −45 and 120° C. (FIG. 37). The presence of both $T_g$s near that of the respective homopolymers suggests the PAMI and PnBA domains are microphase separated, an essential feature for thermoplastic elastomer applications.

TABLE 1

PAMI-CTA and PAMI-b-PnBA sample information.

| Sample | $[M]_0/$ $[CTA]_0$ | Conv. (%)[a] | $M_n$ (NMR) (kg mol$^{-1}$)[b] | $M_n$ (SEC) (kg mol$^{-1}$)[c] | $M_n$ (calc.) (kg mol$^{-1}$)[d] | $M_n$ (calc.)/ $M_n$ (SEC) | $M_n$ (calc.)/ $M_n$ (NMR) | Đ[c] |
|---|---|---|---|---|---|---|---|---|
| PAMI-CTA (14) | 40 | 95 | 11.8 | 13.8 | 10.1 | 0.73 | 0.86 | 1.07 |
| PAMI-CTA (17) | 50 | 95 | 15.0 | 16.7 | 12.5 | 0.75 | 0.83 | 1.06 |
| PAMI-CTA (19) | 60 | 95 | 16.9 | 18.7 | 14.9 | 0.80 | 0.88 | 1.09 |
| PAMI-CTA (24) | 80 | 92 | 21.7 | 24.2 | 19.2 | 0.79 | 0.88 | 1.07 |
| PAMI-CTA (31) | 100 | 92 | 28.1 | 30.9 | 23.9 | 0.77 | 0.85 | 1.08 |
| PAMI-b-PnBA (14-69) | 870 | 64 | 82.7 | 88.3 | 85.1 | 0.96 | 1.03 | 1.12 |
| PAMI-b-PnBA (17-55) | 870 | 51 | 71.8 | 70.7 | 73.5 | 1.04 | 1.02 | 1.12 |
| PAMI-b-PnBA (19-60) | 870 | 56 | 78.6 | 85.7 | 81.1 | 0.95 | 1.03 | 1.19 |
| PAMI-b-PnBA (24-54) | 870 | 50 | 80.3 | 78.7 | 79.9 | 1.01 | 1.00 | 1.14 |
| PAMI-b-PnBA (31-56) | 870 | 52 | 87.1 | 102 | 88.8 | 0.87 | 1.02 | 1.24 |

[a]Of monomer, determined by $^1$H NMR spectroscopy
[b]From end group analysis
[c]Determined by SEC-MALLS in THF
[d]Assuming each CTA generates 1 polymer chain Example 4

Block Copolymerization of AMI-CTA Polymer

Figure 20:
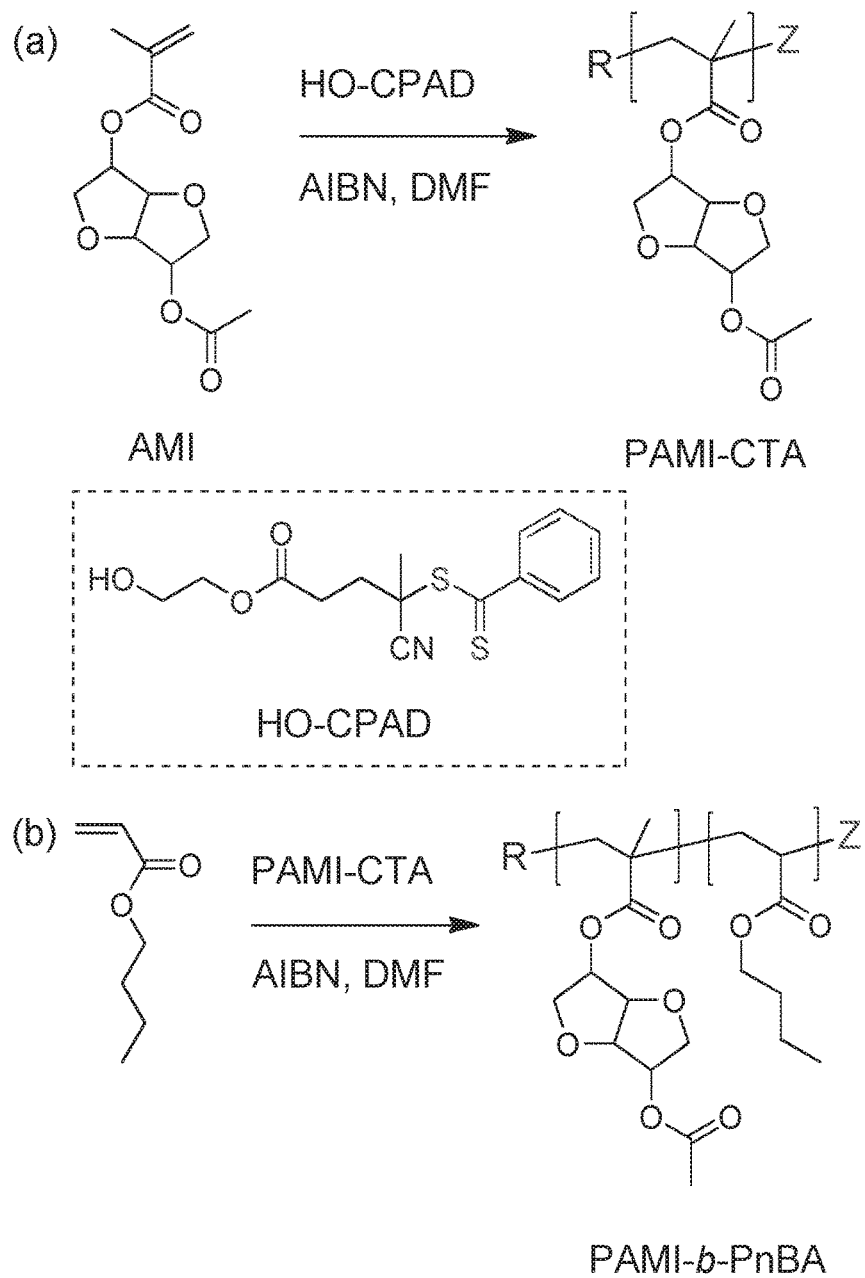
FIG. 20 is a flow diagram of an example reaction scheme for polymerization of AMI to PAMI and chain-transfer agent (PAMI-CTA and to poly acetylated methacrylic isosorbide-block-poly-n-butyl acrylate (PAMI-b-PnBA).
Figure 35:
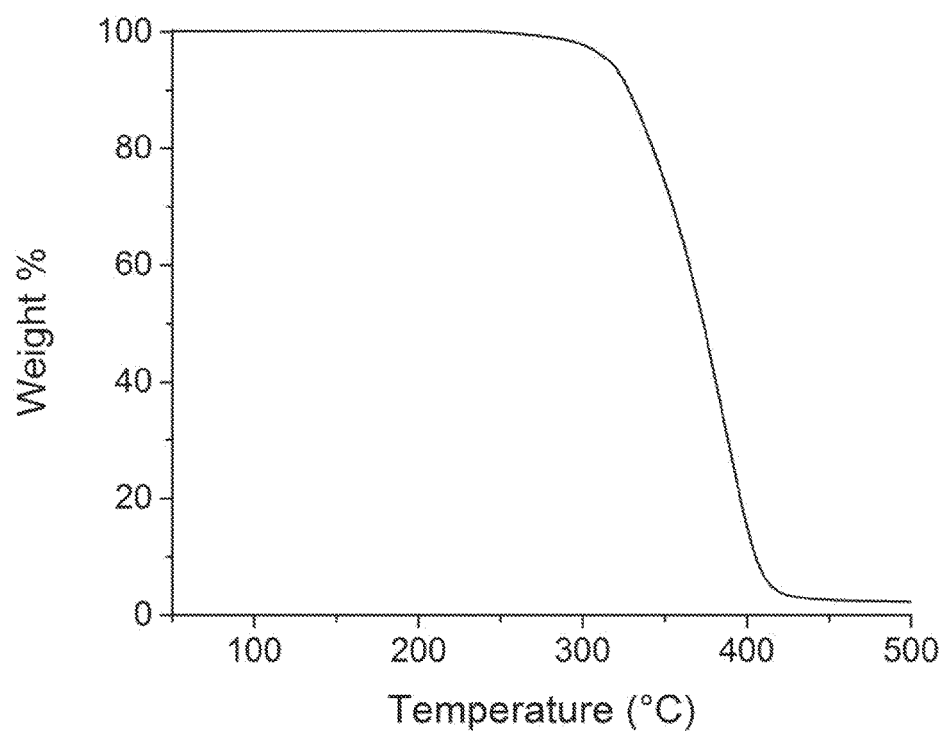
FIG. 35 is a graph of TGA in $N_2$ of PAMI-b-PnBA samples 14-69 at a heating rate of 10° C. $min^{-1}$.
Figure 36:
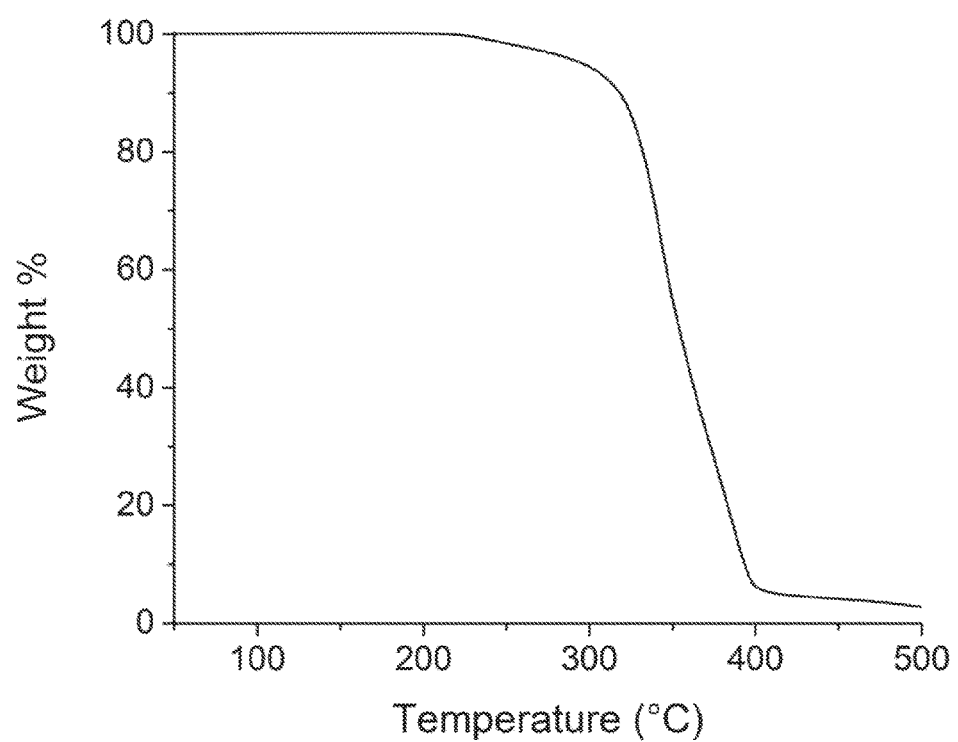
FIG. 36 is a graph of TGA in air of PAMI-b-PnBA samples 14-69 at a heating rate of 10° C. $min^{-1}$.

Chain extension of PAMI-CTA with n-butyl acrylate afforded the block copolymer samples PAMI-b-PnBA (Step b in FIG. 20, Table 3). PnBA is an appealing option for a rubbery counterpart to PAMI due to its low $T_g$ (∼−50° C.) and recent developments towards the commercial production of biobased acrylates. In all cases the PAMI-b-PnBA samples had a broader molar distribution relative to that of PAMI-CTA. Inspection of the SEC traces showed a slight high molar mass shoulder, likely due to termination by combination of propagating radicals (FIGS. 30-34). Termination events are deviations from ideal behavior for controlled radical polymerizations and result in broadened molar mass distributions. TGA of PAMI-b-PnBA showed marked increase in $T_d$ compared to PAMI-CTA (14) homopolymer ($T_d$, 5% weight loss: $N_2$=316 OC, air=296 OC, FIGS. 35 and 36). The higher $T_d$ of PAMI-b-PnBA compared to PAMI is due to the differences in thermal stability and decomposition mechanisms between poly(acrylate)s and poly(methacrylate)s. Poly(acrylate)s undergo thermal decomposition by a random-chain scission mechanism with a $T_d$ ∼310° C. while poly(methacrylate)s decom- Example 5

Synthesis of Acetylated Acrylic Isosorbide (AAI) Monomer

Figure 38:
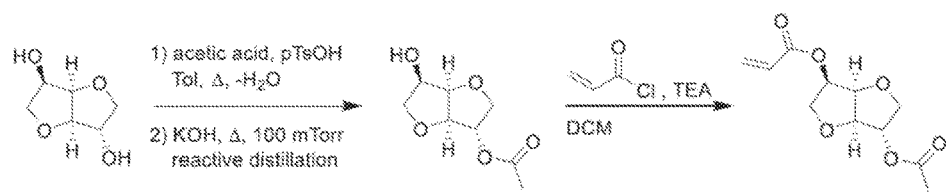
FIG. 38 is a flow diagram of an example reaction scheme for preparing an acetylated acrylic isosorbide (AAI) monomer.

AAI was prepared in two steps according to the reaction scheme shown in FIG. 38. In the first step, isosorbide was reacted with acetic acid in a solvent comprising toluene. The reaction of the isosorbide with acetic acid was performed with added heat and in the presence of p-toluenesulfonic acid as a catalyst. After the primary reaction of the isosorbide with the acetic acid, the reaction mixture was subjected to reactive distillation in the presence of potassium hydroxide under added heat and a pressure of 100 mTorr. The reactive distillation resulted in a yield of about 50% monoacetylated isosorbide, primarily in the form of isosorbide endo-acetate of structure (XII).

In the second step, the monoacetylated isosorbide from the first step was reacted with acryloyl chloride in a solvent include dichloromethane ($CH_2Cl_2$) in the presence of triethylamine (TEA) as a catalyst to provide the acetylated acrylic isosorbide ("AAI") monomer.

Example 6

Free Radical Polymerization of AAI Monomer

Figure 39:
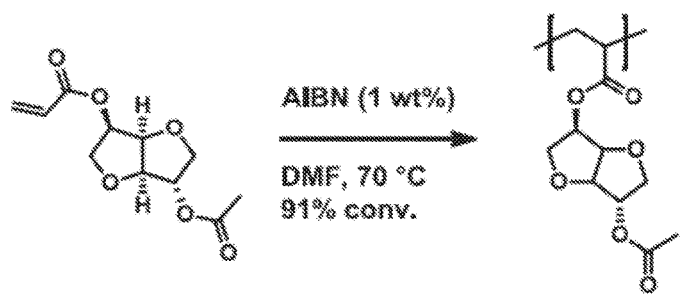
FIG. 39 is a flow diagram of an example reaction scheme for free-radical polymerization of AAI to provide a polyacetylated acrylic isosorbide ("PAMI").

A polyacetylated acrylic isosorbide ("PAAI") polymer was formed via the reaction scheme shown in FIG. 39.

Thermally initiated free-radical polymerization of the AAI monomer from EXAMPLE 5 was carried out in the presence of a 1 wt. % solution of azobisisobutyronitrile (AIBN) at 70° C. in a solvent comprising dimethylformamide ("DMF") to form a polyacetylated acrylic isosorbide ("PAAI"). Analysis of the reaction mixture indicated that 91% conversion of the AAI monomer was achieved within about 2 hours of reaction time.

The number average molar mass ($M_n$) of the resulting PAAI, as measured by size exclusion chromatography in THF with multi-angle laser light scattering detection (SEC-MALLS) was about 120 kg mol$^{-1}$ with $Đ$=4.99. Thermogravimetric analysis (TGA) showed a $T_d$ (5% weight loss) of 332° C. and 290° C. under $N_2$ and air, respectively. The PAAI sample exhibited a glass transition temperature $T_g$ of 95° C. when measured by DSC. This is comparable to commercialized glassy-like polymers, such as polystyrene ($T_g$ ~100° C.) and PMMA ($T_g$ ~110° C.).

Example 7

Block Copolymerization of AAI with N-Butyl Acrylate

Figure 40:
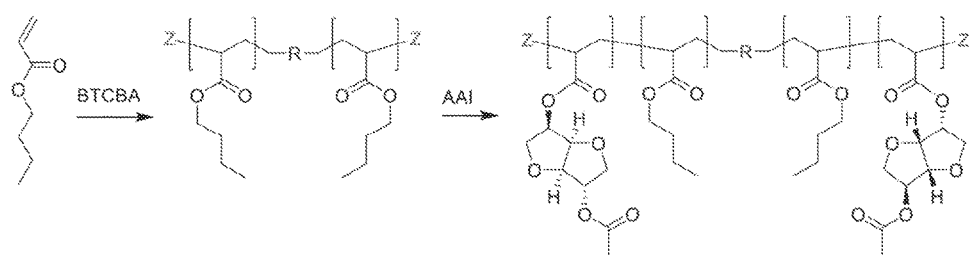
FIG. 40 is a flow diagram of an example reaction scheme for chain-transfer polymerization of AAI and n-butyl acrylate to provide a polyacetylated acrylic isosorbide-block-poly-n-butyl acrylate-block-polyacetylated acrylic isosorbide ("PAAI-b-PnBA-b-PAAI").

A triblock copolymer comprising outer blocks of PAAI and a poly-n-butyl acrylate (PnBA) midblock was prepared according to the reaction scheme shown in FIG. 40. N-butyl acrylate was polymerized via reaction with BTCBA in the presence of a 1 wt. % solution of azobisisobutyronitrile (AIBN) at 70° C. in a solvent comprising dimethylformamide ("DMF") to form a PnBA-BTCBA midblock. The AAI from EXAMPLE 5 was subjected to RAFT polymerization by reacting the AAI with the PnBA-BTCBA midblock in the presence of a 1 wt. % solution of AIBN at 70° C. in a solvent comprising DMF for a reaction time of about 2 hours. The result was the polyacetylated acrylic isosorbide-block-poly-n-butyl acrylate-block-polyacetylated acrylic isosorbide (PAAI-b-PnBA-b-PAAI) of structure (XXXIX).

Three samples of the PAAI-b-PnBA-b-PAAI were prepared, each having different molecular weight.
1) A first sample of the PAAI-b-PnBA-b-PAAI was found to have a number average molar mass ($M_n$), as measured by SEC-MALLS, of about 53.3 kg mol$^{-1}$ with $Đ$=1.09. The weight percentage of the PAAI blocks in the first sample of the PAAI-b-PnBA-b-PAAI, as determined by $^1$H NMR spectroscopy, was about 12 wt. %.
2) A second sample of the PAAI-b-PnBA-b-PAAI was found to have a number average molar mass ($M_n$), as measured by SEC-MALLS, of about 60.2 kg mol$^{-1}$ with $Đ$=1.12. The weight percentage of the PAAI blocks in the second sample of the PAAI-b-PnBA-b-PAAI, as determined by $^1$H NMR spectroscopy, was about 17 wt. %.
3) A third sample of the PAAI-b-PnBA-b-PAAI was found to have a number average molar mass ($M_n$), as measured by SEC-MALLS, of about 69.2 kg mol$^{-1}$ with $Đ$=1.15. The weight percentage of the PAAI blocks in the third sample of the PAAI-b-PnBA-b-PAAI, as determined by $^1$H NMR spectroscopy, was about 21 wt. %.

Example 8

Block Copolymerization of AAI with 2-Ethylhexyl Acrylate

Figure 41:
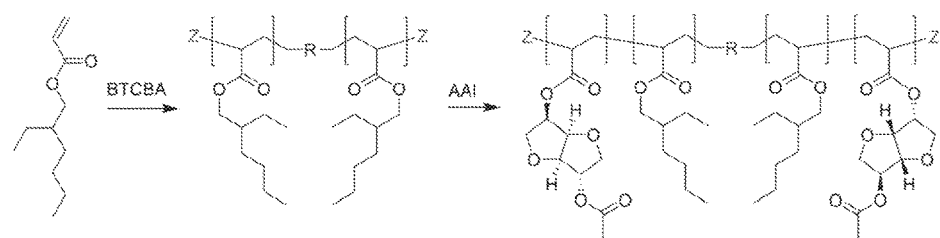
FIG. 41 is a flow diagram of an example reaction scheme for chain-transfer polymerization of AAI and 2-ethylhexyl acrylate to provide a polyacetylated acrylic isosorbide-block-poly-2-ethylhexyl acrylate-block-polyacetylated acrylic isosorbide ("PAAI-b-PEHA-b-PAAI").

A triblock copolymer comprising outer blocks of PAAI and a poly-2-ethylhexyl acrylate (PEHA) midblock was prepared according to the reaction scheme shown in FIG. 41. 2-ethylhexyl acrylate was polymerized via reaction with BTCBA in the presence of a 1 wt. % solution of azobisisobutyronitrile (AIBN) at 70° C. in a solvent comprising DMF to form a PEHA-BTCBA midblock. The AAI from EXAMPLE 5 was subjected to RAFT polymerization by reacting the AAI with the PEHA-BTCBA midblock in the presence of a 1 wt. % solution of AIBN at 70° C. in a solvent comprising DMF for a reaction time of about 2 hours. The result was a polyacetylated acrylic isosorbide-block-poly-2-ethylhexyl acrylate-block-polyacetylated acrylic isosorbide (PAAI-b-PEHA-b-PAAI) of structure (XLII).

The terms and expressions that have been employed are used as terms of description and not of limitation, and there is no intention in the use of such terms and expressions of excluding any equivalents of the features shown and described or portions thereof, but it is recognized that various modifications are possible. Thus, it should be understood that although specific embodiments are described herein with reference to optional features, modification and variation of the concepts described herein may be resorted to by those of ordinary skill in the art, and that such modifications and variations are considered to be within the scope of embodiments of the present invention.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a molding system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to allow the reader to quickly ascertain the nature of the technical disclosure. It is submitted with the understanding that it will not be used to interpret or limit the scope or meaning of the claims.

Although the invention has been described with reference to exemplary embodiments, workers skilled in the art will recognize that changes may be made in form and detail without departing from the spirit and scope of the invention.

What is claimed is:

1. A monomer comprising the structure

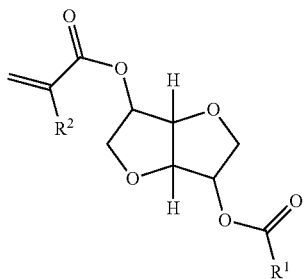

wherein $R^1$ comprises H or a substituted hydrocarbyl or an unsubstituted saturated hydrocarbyl, and wherein $R^2$ comprises H, a halide, or a substituted or unsubstituted hydrocarbyl.

2. The monomer of claim 1, wherein $R^1$ comprises H or a methyl group ($CH_3$).

3. The monomer of claim 1, wherein $R^2$ comprises H or a methyl group ($CH_3$).

4. The monomer of claim 1, wherein the monomer is an acetylated methacrylic isosorbide having the structure

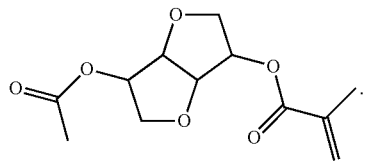

5. A polymer or a copolymer comprising, as a repeating unit, the structure

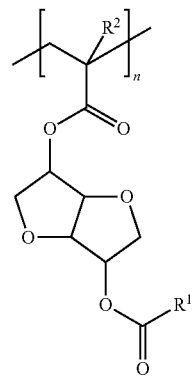

wherein $R^1$ comprises H or a substituted hydrocarbyl, and wherein $R^2$ comprises H, a halide, or a substituted or unsubstituted hydrocarbyl.

6. The polymer or copolymer of claim 5, wherein $R^1$ comprises H or a methyl group ($CH_3$).

7. The polymer or copolymer of claim 5, wherein $R^2$ comprises H or a methyl group ($CH_3$).

8. A method comprising:
(a) reacting a dianhydrohexitol precursor having the structure

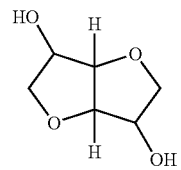

with an acyl-group containing compound having the structure

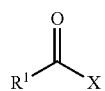

wherein $R^1$ comprises H or a substituted hydrocarbyl or an unsubstituted saturated hydrocarbyl, and X comprises a halide, a hydroxyl group, or an acyl group to form an acylated dianhydrohexitol ester intermediate having the structure

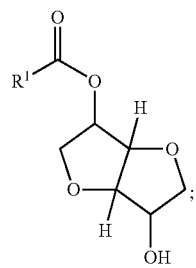

and
(b) reacting the acylated dianhydrohexitol ester intermediate with an acrylic-based compound having the structure

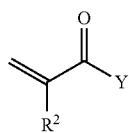

wherein R² comprises H, a halide, or a substituted or unsubstituted hydrocarbyl, and Y comprises a halide, a hydroxyl group, or an acyl group, to form a dianhydrohexitol-based monomer having the structure

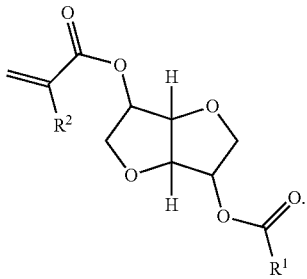

9. The method of claim 8, wherein R¹ comprises H or a methyl group (CH₃).

10. The method of claim 8, wherein R² comprises H or a methyl group (CH₃).

11. The method of claim 8, wherein the dianhydrohexitol-based monomer comprises an acetylated methacrylic isosorbide having the structure

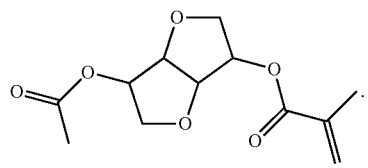

12. A method comprising:
(a) reacting a dianhydrohexitol precursor having the structure

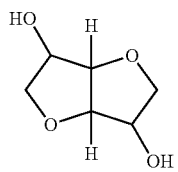

with an acrylic-based compound having the structure

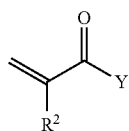

wherein R² comprises H, a halide, or a substituted or unsubstituted hydrocarbyl, and Y comprises a halide, a hydroxyl group, or an acyl group to form an acrylic-based dianhydrohexitol ester intermediate having the structure

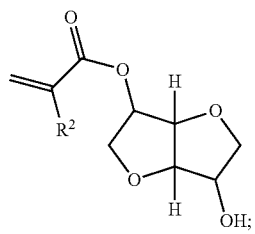

and (b) reacting the acrylic-based dianhydrohexitol ester intermediate with an acyl-group containing compound having the structure

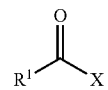

wherein R¹ comprises H or a substituted hydrocarbyl or an unsubstituted saturated hydrocarbyl, and X comprises a halide, a hydroxyl group, or an acyl group, to form a dianhydrohexitol-based monomer having the structure

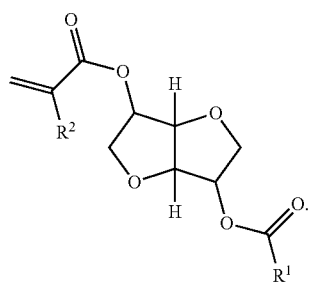

13. The method of claim 12, wherein R¹ comprises H or a methyl group (CH₃).

14. The method of claim 12, wherein R² comprises H or a methyl group (CH₃).

15. The method of claim 12, wherein the dianhydrohexitol-based monomer comprises an acetylated methacrylic isosorbide having the structure

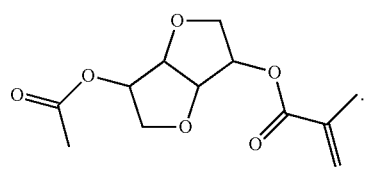 [SMILES: C=C(C)C(=O)OC1COC2C(OC(C)=O)COC12]

16. The method as in either one of claims 8 or 12, further comprising (c) polymerizing the dianhydrohexitol-based monomer to form a polymer or copolymer comprising, as a repeating unit, the structure

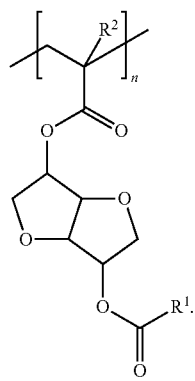

17. The method of claim 16, wherein polymerizing the dianhydrohexitol-based monomer comprises one of:
   linear chain growth polymerization of the dianhydrohexitol-based monomer;
   free-radical polymerization of the dianhydrohexitol-based monomer; or
   controlled block polymerization.

18. The method of claim 16, wherein polymerizing the dianhydrohexitol-based monomer comprises reversible addition-fragmentation chain transfer with a chain-transfer agent to form a chain-transfer polymer.

* * * * *